US011414400B2

(12) United States Patent
Guo et al.

(10) Patent No.: US 11,414,400 B2
(45) Date of Patent: Aug. 16, 2022

(54) METHOD FOR PREPARING SULFONAMIDES DRUGS

(71) Applicants: ASCENTAGE PHARMA (SUZHOU) CO., LTD, Suzhou (CN); ASCENTAGE PHARMA GROUP CORP LIMITED, Hong Kong (CN)

(72) Inventors: Ming Guo, Suzhou (CN); Jianfeng Wen, Suzhou (CN); Tianzhu Wu, Suzhou (CN); Huirong Lu, Suzhou (CN); Feng Xu, Suzhou (CN)

(73) Assignees: ASCENTAGE PHARMA (SUZHOU) CO., LTD., Suzhou (CN); ASCENTAGE PHARMA GROUP CORP LIMITED, Hong Kong (CN)

( * ) Notice: Subject to any disclaimer, the term of this patent is extended or adjusted under 35 U.S.C. 154(b) by 8 days.

(21) Appl. No.: 16/955,013

(22) PCT Filed: Jan. 3, 2020

(86) PCT No.: PCT/CN2020/070164

§ 371 (c)(1),
(2) Date: Jun. 17, 2020

(87) PCT Pub. No.: WO2020/140957

PCT Pub. Date: Jul. 9, 2020

(65) Prior Publication Data

US 2021/0221788 A1 Jul. 22, 2021

(30) Foreign Application Priority Data

Jan. 4, 2019 (WO) ................ PCT/CN2019/070514

(51) Int. Cl.
*C07D 401/12* (2006.01)
*C07D 207/36* (2006.01)

(52) U.S. Cl.
CPC ......... *C07D 401/12* (2013.01); *C07D 207/36* (2013.01)

(58) Field of Classification Search
CPC .................................................... C07D 401/12
See application file for complete search history.

(56) References Cited

U.S. PATENT DOCUMENTS

| | | | |
|---|---|---|---|
| 2012/0189539 | A1 | 7/2012 | Wang |
| 2014/0199234 | A1 | 7/2014 | Wang |
| 2019/0367496 | A1 | 12/2019 | Beausoleil |

FOREIGN PATENT DOCUMENTS

| | | | | |
|---|---|---|---|---|
| CN | 103562202 | A | | 2/2014 |
| CN | 105246882 | A | | 1/2016 |
| CN | 110662752 | A | | 1/2020 |
| WO | WO2010/027431 | | * | 3/2010 |
| WO | WO2010027431 | A1 | | 3/2010 |
| WO | WO2012/103059 | | * | 8/2012 |
| WO | WO2012103059 | A2 | | 8/2012 |
| WO | WO2014/032801 | | * | 3/2014 |
| WO | WO2014032801 | A1 | | 3/2014 |
| WO | WO2014/113413 | | * | 7/2014 |
| WO | WO2014113413 | A1 | | 7/2014 |
| WO | WO2019213151 | A1 | | 11/2019 |

OTHER PUBLICATIONS

International Search Report and Written Opinion dated Mar. 26, 2020, for PCT Application No. PCT/CN2020/070164, filed on Jan. 3, 2020, 17 pages.
Aguilar, A. et al. (Apr. 11, 2013). "A Potent and Highly Efficacious Bcl-2/Bcl-xL Inhibitor," J. Med. Chem. 56(7):3048-3067, 44 pages.
Zhou, H. et al. (Jul. 12, 2012). "Structure-Based Design of Potent Bcl-2/Bcl-xL Inhibitors With Strong in vivo Antitumor Activity," J. Med. Chem. 55(13):6149-6161, 31 pages.

* cited by examiner

*Primary Examiner* — Paul V Ward
(74) *Attorney, Agent, or Firm* — Morrison & Foerster LLP

(57) ABSTRACT

The present invention relates to a method for preparing sulfonamides which are inhibitors of Bcl-2/Bcl-xL, comprising the compound (3R)-1-(3-(4-(4-(4-(3-(2-(4-chlorophenyl)-1-isopropyl-4-methylsulfonyl-5-methyl-1H-pyrrol-3-yl)-5-fluorophenyl)piperazin-1-yl)-phenylaminosulfonyl)-2-trifluoro methylsulfonyl-anilino)-4-phenylthio-butyl)-4-hydroxyl-piperidine, and the present invention also relates to intermediates for the preparation of the sulfonamides, a new final product and its therapeutic use, and pharmaceutical use.

11 Claims, No Drawings

METHOD FOR PREPARING SULFONAMIDES DRUGS

CROSS REFERENCE TO RELATED APPLICATIONS

This application is a National Phase filing under 35 U.S.C. § 371 of International Application No. PCT/CN2020/070164, having an International Filing Date of Jan. 3, 2020, which claims priority benefit of PCT/CN2019/070514, filed Jan. 4, 2019.

TECHNICAL FIELD

The present invention relates to a method for preparing sulfonamides drugs (referred to as sulfonamides for simplicity) which are inhibitors for Bcl-2/Bcl-xL, especially relates to (3R)-1-(3-(4-(4-(4-(3-(2-(4-chlorophenyl)-1-isopropyl-4-methylsulfonyl-5-methyl-1H-pyrrol-3-yl)-5-fluorophenyl)piperazin-1-yl)-phenylaminosulfonyl)-2-trifluoro methylsulfonyl-anilino)-4-phenylthio-butyl)-4-hydroxyl-piperidine, and the present invention also relates to an intermediate for preparing the sulfonamide, a new end product and its pharmaceutical uses.

BACKGROUND ART

Compound (3R)-1-(3-(4-(4-(4-(3-(2-(4-chlorophenyl)-1-isopropyl-4-methyl-sulfonyl-5-methyl-1H-pyrrol-3-yl)-5-fluorophenyl)piperazin-1-yl)-phenylaminosulfonyl)-2-trifluoromethylsulfonyl-anilino)-4-phenylthio-butyl)-4-hydroxyl-piperidine (hereinafter abbreviated as Compound 1) is a sulfonamide which can be used as a Bcl-2/Bcl-xL inhibitor, and its structural formula is as follows.

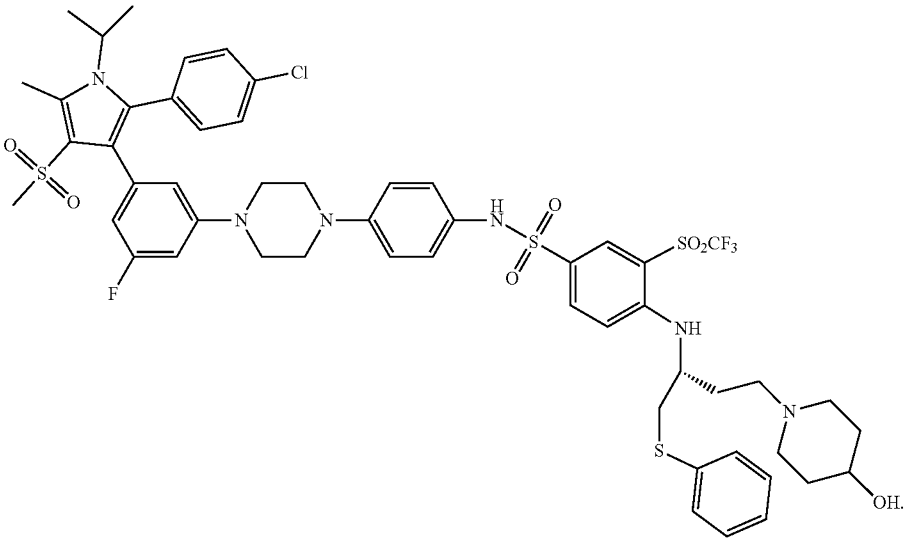

Compound 1 is a potential inhibitor for Bcl-2 and/or Bcl-xL (see U.S. Pat. No. 8,691,184B). The compound is effective in inducing apoptosis of cancer cells and has a mechanism of action that is highly consistent with targeting Bcl-2 and Bcl-xL, which can treat various cancers including, but not limited to, bladder cancer, breast cancer, colon cancer, kidney cancer, liver cancer, lung cancer, ovarian cancer, prostate cancer, testicular cancer, genitourinary tract cancer, lymphatic system cancer, rectal cancer, laryngeal cancer, pancreatic cancer, esophageal cancer, stomach cancer, gallbladder cancer, cervical cancer, thyroid cancer, renal cancer and skin cancer; hematopoietic tumors of lymphoid system; hematopoietic tumors of myeloid lineage; tumors of central and peripheral nervous system; tumors of interstitial origin; and other tumors.

U.S. Pat. No. 8,691,184B (hereinafter referred to as Patent 1 for simplicity) discloses a method for preparing Compound 1, using a dangerous reagent such as n-BuLi, requiring severe temperature control conditions, such as a low temperature condition of −78° C., which has safety hazards and produces toxic by-products, causing environmental pollution, using solvents that are prone to environmental pollution, having high cost, long cycle, low total yield and limited batch capacity. Compound 1 is obtained by a high-performance liquid phase preparation, which is costly and unsuitable for production on a large scale.

Therefore, there is an urgent need for a method for preparing Compound 1, which is suitable for production on a large scale, can solve the technical problems existing in the prior art. The method can avoid the use of dangerous reagents, such as n-BuLi and Pd/C, as well as severe temperature control conditions, such as low temperature conditions of −78° C., produce no or less toxic by-products, use no or less solvents that are prone to environmental pollution, reduce emissions of organic solvent waste, reduce or eliminate the use of column chromatography purification, reduce or eliminate the use of liquid phase purification and freeze-drying operations, reduce costs, shorten cycle time, increase yield, and increase batch capacity.

SUMMARY OF THE INVENTION

It is an object of the present invention to provide a method for preparing sulfonamides, including the compound of formula (I), in particular Compound 1; the method can avoid the use of dangerous n-BuLi and Pd/C and severe temperature control conditions, for example low temperature conditions of −78° C., use safer reagents, such as iron powder, Raney-Ni reduction conditions instead of dangerous Pd/C reduction, use no or less severe temperature control conditions, such as, for example, low temperature conditions of −78° C., produce no or less toxic by-products, use no or less solvents that are prone to environmental pollution, reduce or eliminate the use of column chromatography purification, reduce or eliminate the use of liquid phase purification and freeze-drying operations, reduce costs, shorten cycles, elevate yield, and increase batch capacity. The inventors have surprisingly found that the use of two specific preparation methods (i.e., Method I and Method II, as described below) can reduce or eliminate the use of column chromatography purification, reduce or eliminate the use of liquid phase purification and freeze-drying operations, reduce costs, shorten cycle time, elevate yield, and increase batch capacity. The present invention has been completed based on these findings.

Specifically, a first aspect of the invention relates to a method for preparing a compound of the following Formula (I) or a pharmaceutically acceptable salt thereof, 1. A method for preparing a compound of the following Formula (I) or a pharmaceutically acceptable salt thereof, Formula (I)

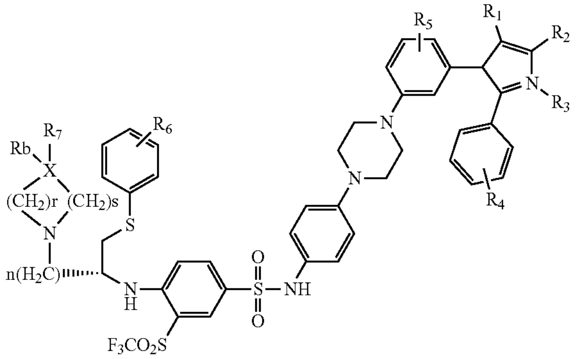

wherein,
$R_1$ is SO2R',
$R_2$ is $C_{1-4}$alkyl,
$R_3$ is $C_{1-4}$alkyl,
$R_4$ is halogen,
$R_5$ is halogen,
$R_6$ is selected from the group consisting of H, halogen, $C_{1-4}$alkyl,
$R_7$ is hydroxyl, $C_{1-4}$alkoxyl or $C_{1-4}$alkoxylcarbonyl,
$R_b$ is hydrogen or $C_{1-4}$alkyl,
n, r and s each are each independently 1, 2, 3, 4, 5 or 6, preferably, r and s each are 2 and n is 3, 4 or 5, more preferably, n, r and s each are 2,
R' is $C_{1-4}$alkyl, more preferably methyl, propyl, isopropyl,
X is carbon or nitrogen, when X is nitrogen, then Rb is H,
the method comprises the following steps:
1) reacting a compound of Formula 1 with a compound of Formula 2 to produce a compound of Formula I, Formula 1

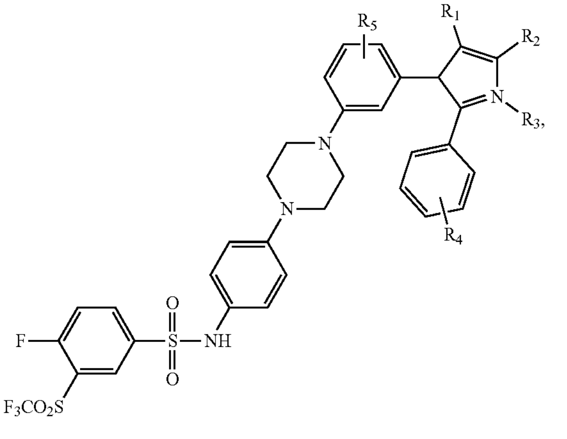

wherein, $R_1$, $R_2$, $R_3$, $R_4$ and $R_5$ each are defined as those for Formula (I);

Formula 2

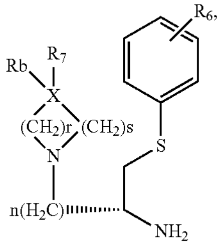

wherein, $R_6$, $R_7$, Rb, r, s and n each are defined as those for Formula (I).

2. The method of the above item 1, wherein $C_{1-4}$alkyl is selected from the group consisting of methyl, propyl or isopropyl; halogen is selected from the group consisting of fluorine, chlorine; and $C_{1-4}$alkoxylcarbonyl is tert-butoxycarbonyl.

3. The method of the above item 1, comprising:

in the step 1), the compound of Formula 2 is in an amount of about 1.5 to 3.0 eq relative to 1 molar equivalent of the compound of Formula 1; and the reaction is performed in the presence of a catalyst such as N,N-diisopropylethylamine (DIPEA), for example about 2.0 to 4.0 eq of DIPEA, and/or in an organic solvent such as DMF.

4. The method of the above item 1, wherein, preparation of the compound of Formula 1 comprises the following steps:

1') reacting a compound of Formula 1' with a compound of Formula 2' to produce a compound of Formula 1, Formula 1'

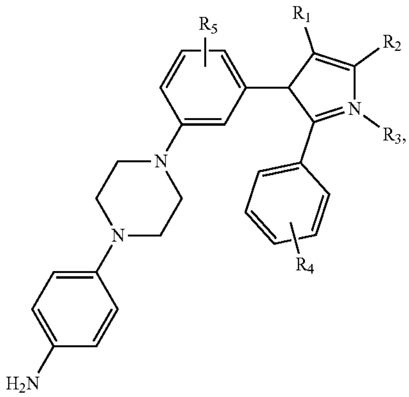

wherein, $R_1$, $R_2$, $R_3$, $R_4$ and $R_5$ each are defined as those for Formula (I);

Formula 2'

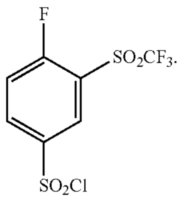

5. The method of the above item 4 comprising one or more of the following characteristics:

in the step 1'), the compound of Formula 2' has a molar equivalent of about 1.5 to 3.0 eq relative to 1 molar equivalent of the compound of Formula 1';

In the step 1'), the reaction is carried out in a polar solvent or a mixture of a plurality of polar solvents, preferably tetrahydrofuran, or a mixture of tetrahydrofuran and dichloromethane;

in the step 1'), the reaction is carried out in the presence of an organic base;

in the step 1'), the reaction is carried out at a temperature ranging from about −10° C. to 10° C.

6. The method of the above item 4 or 5, comprising one or more of the following characteristics:

preparation of the compound of Formula 1' comprises the following steps:

1") reacting a compound of Formula 1" with an alkyl sulfonate salt (e.g., $R_1Na$) to produce a compound of Formula 2", Formula 1″

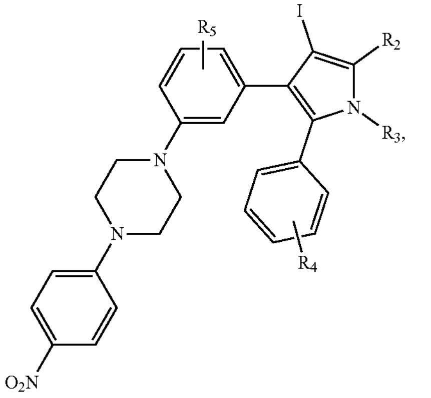

in Formula 1", $R_2$, $R_3$, $R_4$ and $R_5$ each are defined as those for Formula (I);

Formula 2″

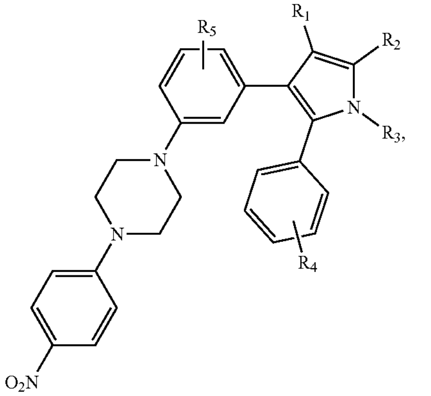

in Formula 2", $R_1$, $R_2$, $R_3$, $R_4$ and $R_5$ each are defined as those for Formula (I);

2") producing the compound of Formula 1' from the compound of Formula 2".

7. The method of the above item 6, comprising one or more of the following characteristics:

in the step 1"), the alkyl sulfonate salt (for example, $R_1Na$) is used in an amount of about 10 to 15 eq, relative to 1 molar equivalent of the compound of the Formula 1;

in the step 1"), the reaction is carried out in the presence of a catalyst such as metal iodide in an amount of about 0.5 to 1.0 eq, L-proline in an amount of about 1.0-1.3 eq, relative to 1 molar equivalent of the compound of the Formula 1", and an alkali metal hydroxide, and/or in an organic solvent, at about 80-110° C.; and/or in the step 2"), a catalyst is used, which is selected from the group consisting of Raney nickel, iron powder;

in the step 2"), the reaction is carried out in a polar solvent such as tetrahydrofuran.

8. The method of the above item 6 or 7, comprising one or more of the following characteristics:

preparation of the compound of Formula 1" comprises the following steps: 1"') reacting a compound of Formula 1"' with a compound of Formula 2"' to form a compound of Formula 3"', Formula 1‴

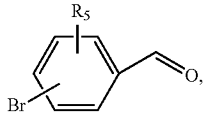

in Formula 1, $R_5$ is defined as that for Formula (I);

Formula 2‴

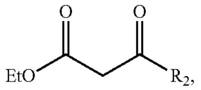

in Formula 2"', $R_2$ is defined as that for Formula (I);

Formula 3‴

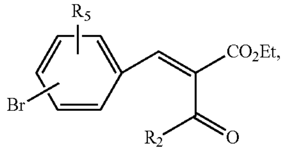

in Formula 3"', $R_2$ and $R_5$ are defined as those for Formula (I); 2"') reacting the compound of Formula 3"' with a compound of Formula 4"' to form a compound of Formula 5"', Formula 4‴

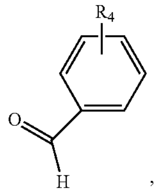

in Formula 4"', $R_4$ is defined as that for Formula (I);

Formula 5‴

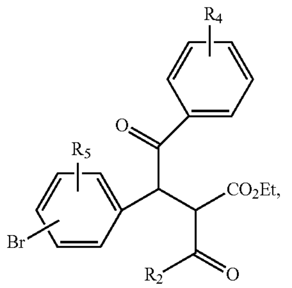

in Formula 5"', $R_2$, $R_4$ and $R_5$ each are defined as those for Formula (I);

3"') reacting the compound of Formula 5"' with a compound of Formula 6"' to form a compound of Formula 77, Formula 6'''

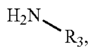

in Formula 6''', $R_3$ is defined as that for Formula (I);

Formula 7'''

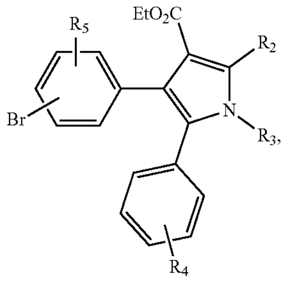

in Formula 7''', $R_2$, $R_3$, $R_4$ and $R_5$ each are defined as those for Formula (I);

4''') forming a compound of Formula 8'' from the compound of Formula 7''',

Formula 8'''

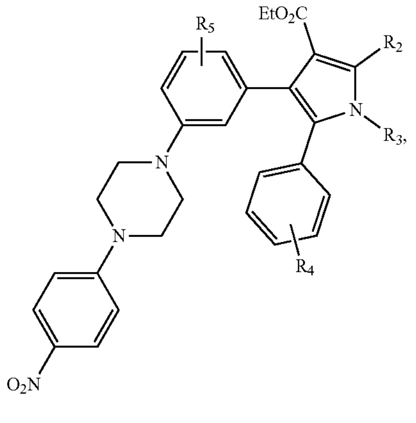

in Formula 8''', $R_2$, $R_3$, $R_4$ and $R_5$ each are defined as those for Formula (I);

5''') forming a compound of Formula 9''' from the compound of Formula 8''',

Formula 9'''

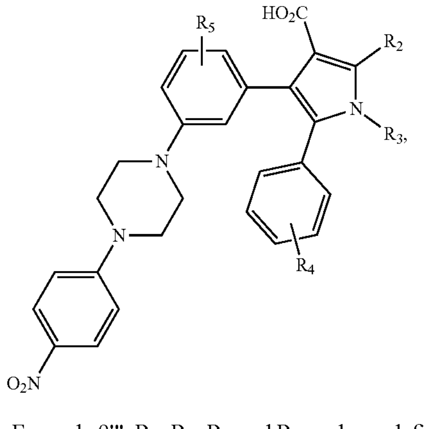

in Formula 9''', $R_2$, $R_3$, $R_4$ and $R_5$ each are defined as those for Formula (I);

6''') forming a compound of Formula 10''' from the compound of Formula 9''',

Formula 10'''

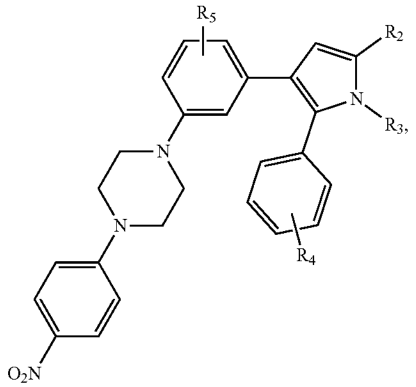

in Formula 10''', $R_2$, $R_3$, $R_4$ and $R_5$ each are defined as those for Formula (I);

7''') forming the compound of Formula 1'' from the compound of Formula 10'''.

9. The method of the above item 8, wherein, in Formula 1''', Formula 3''', Formula 5''' and Formula 7''', phenyl ring is substituted in the meta position by $R_5$, or phenyl ring is substituted in the meta positions by $R_5$ and Br.

10. The method of the above item 8 or 9, comprising one or more of the following characteristics:

in the step 1'''), the concentration of the compound of Formula 1''' in the organic solvent is about 0.4 to 0.5 M;

in the step 1'''), the reaction is carried out in the presence of an organic base such as tetrahydropyrrole, piperidine, and/or in the presence of AcOH, and/or in an organic solvent, under reflux, for about 18-20 hours;

in the step 2'''), the reaction is carried out in the presence of an organic base, 3-ethyl-5-(2-hydroxyethyl)-4-methylthiazolium bromide, and/or in the presence of a polar solvent, at 60-80° C., preferably about 70° C., for 18-20 hours;

in the step 3'''), the amount of the compound of Formula 6''' is 8-15 eq relative to the compound of Formula 5''';

the step 3''') is carried out in a polar solvent, preferably methanol, ethanol, isopropanol;

the step 3''') is carried out in the presence of AcOH, preferably in the presence of about 10 eq of AcOH relative to the compound of Formula 5''', and/or at 40-70° C., for example 50° C., for about 18-20 hours;

in the step 4'''), the compound of Formula 7''' reacts with 1-(nitrophenyl)piperazine, preferably about 1.8 to 2 eq of 1-(nitrophenyl)piperazine relative to the compound of Formula 7''';

the step 4''') is carried out in the presence of a catalyst such as metal iodide, L-proline, carbonate salt, and/or in an organic solvent at 110-130° C. for about 18-20 hours;

in the step 5'), the reaction is carried out in the presence of an excess of a base such as an hydroxide;

in the step 5'''), the reaction is carried out in a mixed solvent such as dioxane:ethanol:water=1:1:1;

in the step 5'''), the reaction is carried under reflux for about 40-50 hours;

the step 6''') is carried out in TFA and DCM for about 30 minutes to 1 hour;

the step 7''') is carried out in the presence of N-iodosuccinimide (NIS), and/or in an organic solvent, at 0° C. to RT;

the steps 1') and 2'') are carried out in a one-pot process.

11. The method of the above item 4 or 5, comprising one or more of the following characteristics:

in the step 1''), the alkyl sulfonate salt (for example, $R_1Na$) is used in an amount of about 10 to 15 eq, relative to 1 molar equivalent of the compound of Formula 1;

in the step 1"), the reaction is carried out in the presence of a catalyst such as metal iodide in an amount of about 0.5 to 1.0 eq, L-proline in an amount of about 1.0-1.3 eq, relative to 1 molar equivalent of the compound of Formula 1", in the presence of an alkali metal hydroxide, and/or in an organic solvent, at 80-110° C.;

in the step (2"), a catalyst is used, which is selected from the group consisting of Raney nickel, iron powder;

the step (2") is carried out in a polar solvent such as ethanol or isopropanol.

12. The method of the above item 11, comprising one or more of the following characteristics:

preparation of the compound of Formula 1" comprises the following steps:

(1''') reacting a compound of Formula 1''' with a compound of Formula 2''' to form a compound of Formula 3''', Formula 1'''

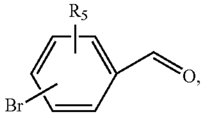

in the Formula 1''', $R_5$ is defined as that for Formula (I);

Formula 2'''

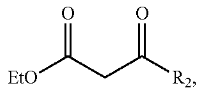

in the Formula 2''', $R_2$ is defined as that for Formula (I);

Formula 3'''

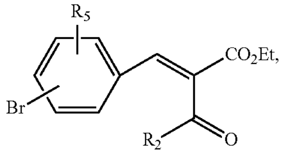

in the Formula 3''', $R_2$ and $R_5$ are defined as those for Formula (I);

2''') reacting the compound of Formula 3''' with a compound of Formula 4''' to form a compound of Formula 5''', Formula 4'''

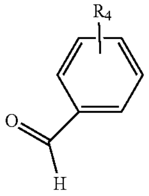

in the Formula 4''', $R_4$ is defined as that for Formula (I);

Formula 5'''

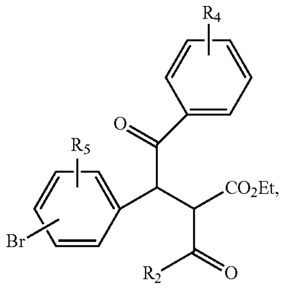

in the Formula 5''', $R_2$, $R_4$ and $R_5$ each are defined as those for Formula (I);

3''') reacting the compound of Formula 5''' with a compound of Formula 6''' to form a compound of Formula 7''', Formula 6'''

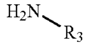

in the Formula 6''', $R_3$ is defined as that for Formula (I);

Formula 7'''

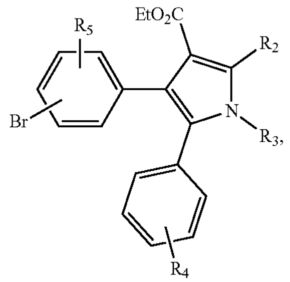

in the Formula 7''', $R_2$, $R_3$, $R_4$ and $R_5$ each are defined as those for Formula (I);

4'''-a) forming a compound of Formula 11''' from the compound of Formula 7''',

Formula 11'''

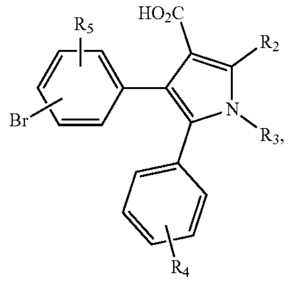

in the Formula 11''', $R_2$, $R_3$, $R_4$ and $R_5$ each are defined as those for Formula (I);

5'''-a) forming a compound of Formula 12''' from the compound of Formula 11''',

Formula 12'''

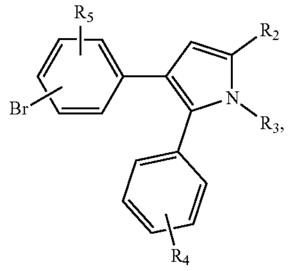

in the Formula 12''', $R_2$, $R_3$, $R_4$ and $R_5$ each are defined as those for Formula (I);

6'''-a) forming a compound of Formula 10''' from the compound of Formula 12''',

Formula 10'''

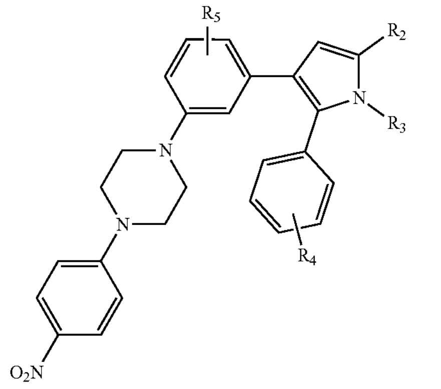

in the Formula 10''', $R_2$, $R_3$, $R_4$ and $R_5$ each are defined as those for Formula (I);

7''') forming a compound of Formula 1'' from the compound of Formula 10'''.

13. The method of the above item 11, wherein, in Formula 3''', Formula 5''', Formula 7''', Formula 11''' and Formula 12''', phenyl ring is substituted in the meta position by $R_5$, or phenyl ring is substituted in the meta positions by $R_5$ and Br.

14. The method of any one of the above items 10-13, comprising one or more of the following characteristics:

in the step 1'''), the reaction is carried out in the presence of an organic base such as piperidine and/or an organic acid such as AcOH, and/or in an organic solvent, under reflux, for 18-20 hours;

the step 2''') is carried out in the presence of an organic base such as triethylamine, 3-ethyl-5-(2-hydroxyethyl)-4-methylthiazolium bromide, and/or in a polar solvent, at about 60-80° C., for 18-20 hours;

in the step 3'''), the amount of the compound of Formula 6''' is about 8-15 eq, relative to 1 molar equivalent of the compound of Formula 5''';

the step 3''') is carried out in a polar solvent;

the step 3''') is carried out in the presence of AcOH, and/or at about 40-70° C., for about 18-20 hours;

the step 4'''-a) is carried out in the presence of a base;

the step 4'''-a) is carried out in a mixed solution of polar solvents such as 1,4-dioxane, ethanol and water;

the step 5'''-a) is carried out in an organic solvent;

the step 5'''-a) is carried out in the presence of a strong acid such as hydrochloric acid, sulfuric acid or trifluoroacetic acid;

in the step 6'''-a), the compound of Formula 12''' reacts with 1-(nitrophenyl)piperazine;

the step 6'''-a) is carried out in the presence of a catalyst such as metal iodide, [(2,6-dimethylphenyl)amino](oxo)acetic acid (DMPAO), carbonate salt;

the step 7''') is carried out in N-iodosuccinimide (NIS), and/or in DMF, at 0° C. to RT.

15. A compound of one of the following Formulae,

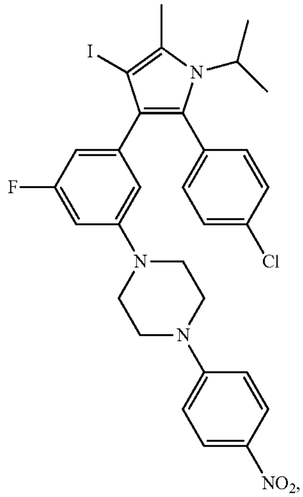

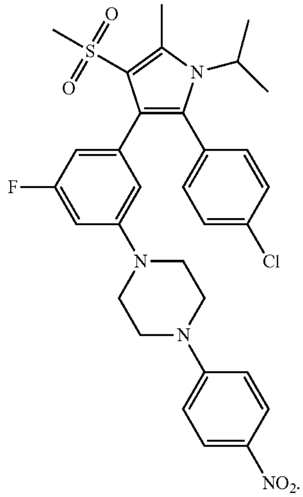

16. Use of the compound of the above item 15 as an intermediate for the preparation of a compound of Formula (I).

The invention also relates to the intermediate compounds prepared in the above preparation methods and the use of the intermediate compounds for preparing the formula (I) compound.

Definition

The term "about" as used herein refers to 10%, more preferably ±5%, and most preferably ±2% of the value modified by the term, so that one of ordinary skill in the art can clearly determine the scope of the term "about" according to the modified value.

Meanings of Symbols iPr refers to isopropyl.

DCM refers to dichloromethane.

THE refers to tetrahydrofuran.

eq refers to molar ratio.

M refers to molar concentration. In the text, the unit of molar concentration is mol/L unless otherwise defined.

TLC refers to thin layer chromatography.

DMF refers to dimethylformamide.

SM refers to the starting material.

Raney-Ni refers to Raney Nickel.

DETAILS OF THE INVENTION

A first aspect of the invention relates to a method for preparing a compound of the Formula (I) or a pharmaceutically acceptable salt thereof (hereinafter referred to as Method I), Formula (I)

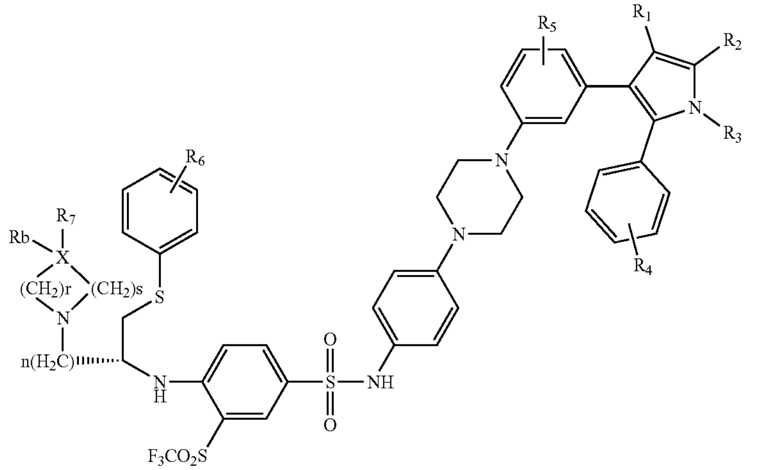

wherein, $R_1$ is SO2R', $R_2$ is an alkyl, preferably $C_{1-4}$alkyl, more preferably methyl, propyl, isopropyl, $R_3$ is an alkyl, preferably $C_{1-4}$alkyl, more preferably methyl, propyl, isopropyl, $R_4$ is a halogen, preferably fluorine, chlorine, $R_5$ is a halogen, preferably fluorine, chlorine, $R_6$ is selected from the group consisting of H, halogen, alkyl, preferably fluorine, chlorine, $C_{1-4}$alkyl, more preferably methyl, propyl, isopropyl, $R_7$ is hydroxyl, alkoxyl, preferably $C_{1-4}$alkoxyl or alkoxylcarbonyl, preferably $C_{1-4}$alkoxylcarbonyl, more preferably butoxycarbonyl, most preferably tert-butoxycarbonyl, $R_b$ is hydrogen or alkyl, preferably $C_{1-4}$alkyl, more preferably methyl, propyl, isopropyl, n, r and s independently are 1, 2, 3, 4, 5 or 6, preferably, r and s both are 2 and n is 3, 4 or 5, more preferably, n, r and s each are 2, R' is an alkyl, preferably $C_{1-4}$alkyl, more preferably methyl, propyl, isopropyl, X is carbon or nitrogen, when X is nitrogen, Rb is H, The above method comprises the following steps:

1) reacting a compound of Formula 1 with a compound of Formula 2 to form a compound of Formula I, Formula 2

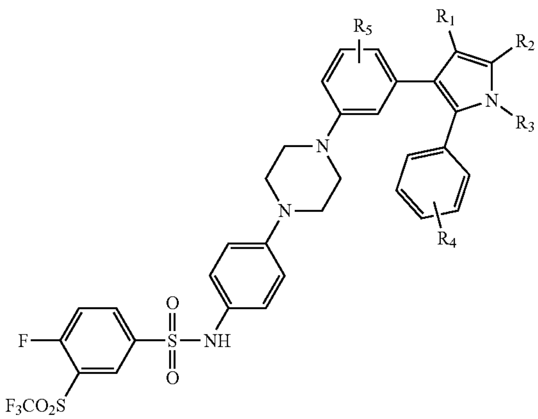

wherein, $R_1$, $R_2$, $R_3$, $R_4$ and $R_5$ each are defined as those for Formula (I);

Formula 2

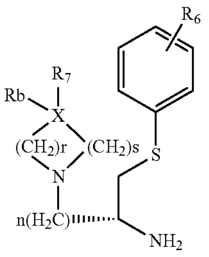

wherein, $R_6$, $R_7$, Rb, r, s and n each are defined as those for Formula (I).

In some embodiments, in step 1), relative to 1 molar equivalent (eq) of the compound of Formula 1, the compound of Formula 2 is about 1.5 to 3.0 eq, preferably about 1.5 to 2.0 eq; the reaction is carried out in the presence of an organic base such as triethylamine, N-methylmorpholine, N,N-diisopropylethylamine (DIPEA), preferably about 2.0 to 4.0 eq, more preferably about 3.0 eq of DIPEA, and/or in an organic solvent such as ethylene glycol dimethyl ether, dimethylsulfoxide and dimethylformamide, preferably dimethylformamide.

In some embodiments, preparation of the compound of Formula 1 comprises the following steps:

1') reacting a compound of Formula 1' with a compound of Formula 2' to form a compound of Formula 1, Formula 1′

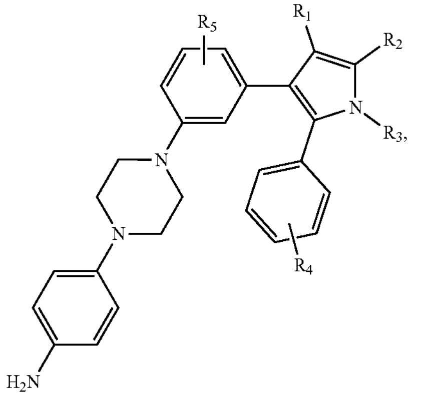

wherein, $R_1$, $R_2$, $R_3$, $R_4$ and $R_5$ each are defined as those for Formula (I);

Formula 2′

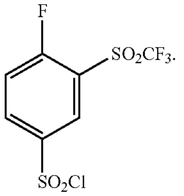

Wherein, the compound of Formula 2' has a molar equivalent of about 1 to 2.5 eq, preferably about 1.5 to 2.0 eq, relative to 1 molar equivalent of the compound of Formula 1'.

In some embodiments, the step 1') is carried out in a polar solvent such as tetrahydrofuran, or a mixture of two or more polar solvents such as tetrahydrofuran and dichloromethane, preferably, carried out in a mixture of tetrahydrofuran and dichloromethane.

In some embodiments, in the step 1'), the concentration of the compound of Formula 1' is 0.01-0.03 M, more preferably 0.02 M.

In some embodiments, the step 1') is carried out in the presence of an organic base, for example in the presence of pyridine, triethylamine, N-methylmorpholine, and diisopropylethylamine, for example, in the presence of pyridine in an amount of about 1.0 eq to 3.0 eq, preferably about 1.5-2.5 eq, relative to 1 eq of the compound of Formula 1'.

In some embodiments, the step 1') is carried out at a temperature of about −10° C. to 10° C., preferably in the range of about −10° C. to 0° C.

In some embodiments, preparation of the compound of Formula 1' comprises the following steps:

1") reacting the compound of Formula 1" with an alkyl sulfonate salt (e.g., $R_1$Na) to form a compound of Formula 2", Formula 1″

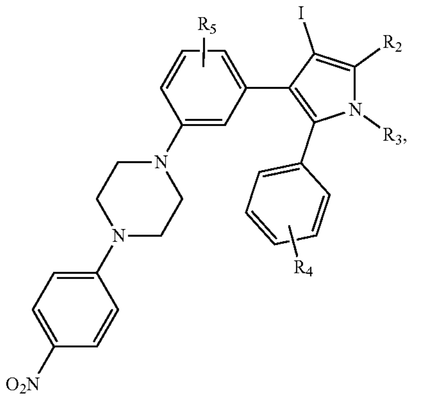

wherein, $R_2$, $R_3$, $R_4$ and $R_5$ each are defined as those for Formula (I);

Formula 2″

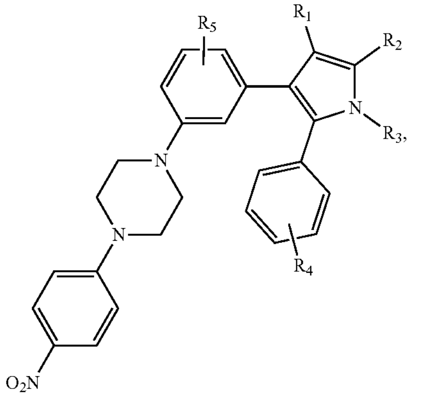

wherein, $R_1$, $R_2$, $R_3$, $R_4$ and $R_5$ each are defined as those for Formula (I);

2") forming a compound of Formula 1' from the compound of Formula 2".

In some embodiments, in the step 1"), the alkyl sulfonate salt (e.g., $R_1$Na) is about 10 to 15 eq, preferably about 10 to 12 eq, relative to 1 eq of the compound Formula 1". Further, the step 1") is carried out in the presence of a catalyst, such as metal iodide, preferably CuI, preferably CuI in an amount of about 0.5 to 1.0 eq, preferably about 0.6 to 0.8 eq, relative to the compound of Formula 1", L-proline, preferably L-proline in an amount of about 0.5 to 1.5 eq, relative to the compound of Formula 1", a base such as a hydroxide, preferably alkali metal hydroxide such as NaOH, KOH, for example, alkali metal hydroxide such as NaOH or KOH in an amount of about 1.5 eq to 2.5 eq (preferably about 2.0 eq), relative to the compound of Formula 1", and/or in an organic solvent such as DMSO, (preferably, the concentration of the compound of Formula 1" in the aforementioned solvent is 0.14-0.25 g/ml), at 80° C. to 110° C., preferably at 90° C. to 100° C.

In some embodiments, the step 2") employs a catalyst such as Raney nickel (e.g. 1.0-3.0 g/g of the compound of Formula 2"), iron powder, more preferably, Raney nickel.

In some embodiments, the step 2") is carried out in a polar solvent, preferably tetrahydrofuran (e.g. 1 eq).

In some embodiments, preparation of the compound of Formula 1" comprises the following steps:

1''') reacting a compound of Formula 1''' with a compound of Formula 2''' to form a compound of Formula 3''', Formula 1'''

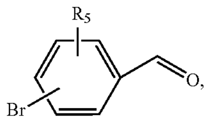

in Formula 1''', $R_5$ is defined as that for Formula (I); preferably phenyl ring is substituted in the meta position by $R_5$, more preferably phenyl ring is substituted in the meta positions by $R_5$ and Br, Formula 2'''

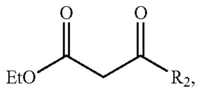

$R_2$ are defined as those for Formula (I);

Formula 3'''

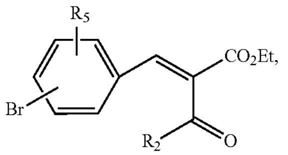

in Formula 3''', $R_2$ and $R_5$ are defined as those for Formula (I); preferably phenyl ring is substituted in the meta position by $R_5$, more preferably phenyl ring is substituted in the meta positions by $R_5$ and Br, 2''') reacting the compound of Formula 3''' with a compound of Formula 4''' to form a compound of Formula 5''', Formula 4'''

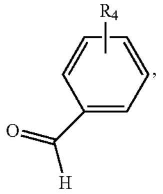

$R_4$ is defined as that for Formula (I);

Formula 5'''

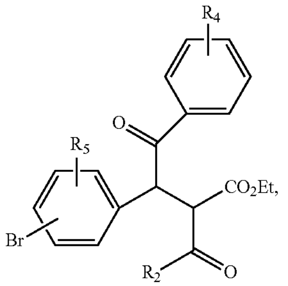

in Formula 5''', $R_4$ and $R_5$ each are defined as those for Formula (I); preferably phenyl ring is substituted in the meta position by $R_5$, more preferably phenyl ring is substituted in the meta positions by $R_5$ and Br, 3''') reacting the compound of Formula 5''' with a compound of Formula 6''' to form a compound of Formula 7''', Formula 6'''

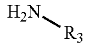

wherein, $R_3$ is defined as that for Formula (I);

Formula 7'''

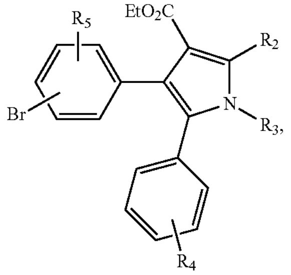

in Formula 7''', $R_2$, $R_3$, $R_4$ and $R_5$ each are defined as those for Formula (I); preferably phenyl ring is substituted in the meta position by $R_5$, more preferably phenyl ring is substituted in the meta positions by $R_5$ and Br, 4''') forming a compound of Formula 8''' from the compound of Formula 7''', Formula 8'''

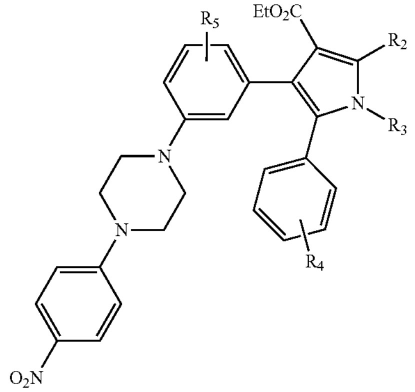

wherein, $R_2$, $R_3$, $R_4$, and $R_5$ are defined as those for Formula (I);

5''') forming a compound of Formula 9''' from the compound of Formula 8''',

Formula 9'''

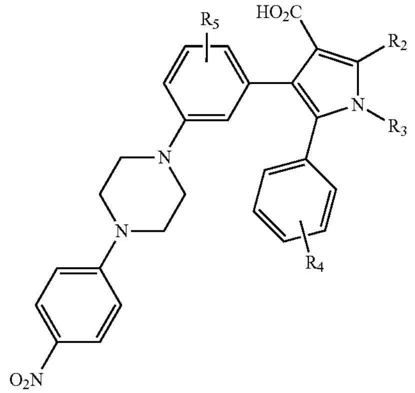

wherein, $R_2$, $R_3$, $R_4$, and $R_5$ are defined as those for Formula (I);

6''') forming a compound of Formula 10''' from the compound of Formula 9''',

Formula 10'''

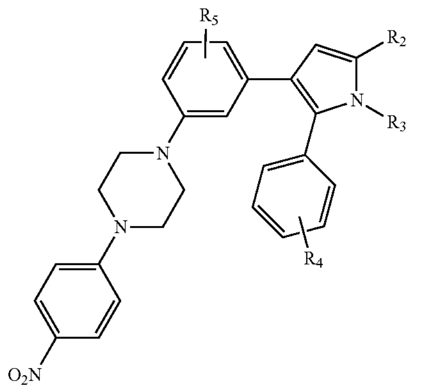

wherein, $R_2$, $R_3$, $R_4$, and $R_5$ are defined as those for Formula (I);

7''') forming a compound of Formula 1'' from the compound of Formula 10'''.

In some embodiments, in the step 1'''), relative to 1.0 eq of the compound of Formula 1''', the concentration of the compound of Formula 1''' in the organic solvent is 0.4 to 0.5 M, the amount of the compound of Formula 2''' is 1.1 eq; the reaction is carried out in the presence of an organic base such as triethylamine, tetrahydropyrrole or piperidine, preferably piperidine in an amount of about 0.01-0.5 ml/g of the compound of Formula 1''', and/or in the presence of AcOH, preferably AcOH in an amount of about 0.03-0.5 ml/g of the compound of Formula 1''', and/or in an organic solvent such as toluene (preferably, the concentration of the compound of Formula 1''' in an organic solvent such as toluene is 1.2 to 1.7 M), under reflux, for about 18-20 hours.

In some embodiments, in the step 2'''), relative to 1 eq of the compound of Formula 3''', the compound of Formula 4''' is used in an amount of about 1 eq.

In some embodiments, the step 2''') is carried out in the presence of an organic base such as triethylamine, tetrahydropyrrole or piperidine, for example triethylamine in an amount of about 1.5-2.5 eq relative to the compound of Formula 3''', 3-ethyl-5-(2-hydroxyethyl)-4-methylthiazolium bromide, such as 3-ethyl-5-(2-hydroxyethyl)-4-methylthiazolium bromide in an amount of about 0.1-0.2 eq relative to compound of Formula 3''', and/or in a polar solvent such as methanol, isopropanol, dimethyl sulfoxide, ethanol, propanol, and/or at about 60-80° C., preferably about 70° C., for 18-20 hours, and/or the concentration of the compound of Formula 3''' in the aforementioned solvent is about 0.6-0.7 M.

In some embodiments, in the step 3'''), the amount of the compound of Formula 6''' is about 8-15 eq, for example about 10 eq, relative to the compound of Formula 5'''.

In some embodiments, the step 3''') is carried out in a polar solvent such as isopropanol, dimethyl sulfoxide, ethanol, methanol.

In some embodiments, the step 3''') is carried out in the presence of an organic acid such as AcOH, preferably AcOH in an amount of about 8-10 eq relative to the compound of Formula 5''', and/or at about 40-70° C. (e.g., 50° C.), for about 18 to 20 hours.

In some embodiments, in the step 4'''), the compound of Formula 7''' reacts with 1-(nitrophenyl)piperazine, preferably 1-(nitrophenyl)piperazine in an amount of about 1.8 to 2 eq relative to the compound of Formula 7'''.

In some embodiments, the step 4''') is carried out in the presence of a catalyst, preferably a metal iodide, more preferably CuI, preferably CuI in an amount of about 0.5 to 1.0 eq, preferably about 0.6 to 0.8 eq, relative to the compound of Formula 7''', L-proline, preferably L-proline in an amount of 0.5-0.7 eq relative to the compound of Formula 7''', a carbonate salt, preferably $K_2CO_3$, preferably $K_2CO_3$ in an amount of 2.5 eq relative to the compound of Formula 7''', and/or in an organic solvent, preferably DMSO (preferably, the concentration of the compound of Formula 7''' in the organic solvent, preferably in DMSO, is 0.2 M), and/or at about 110-130° C., for example about 120° C., and/or 18-20 hours.

In some embodiments, the amount of the compound of Formula 8''' in step 5''') is 1.0 eq.

In some embodiments, the step 5''') is carried out in the presence of a base such as a hydroxide, preferably an alkali metal hydroxide such as NaOH, KOH, for example, NaOH or KOH in an amount of 50 eq relative to the compound of Formula 8'''.

In some embodiments, the step 5''') is carried out in a mixed solvent, more preferably in a mixed solvent of dioxane:ethanol:water=1:1:1, and/or the concentration of the compound of Formula 8''' in the aforementioned mixed solvent is 0.9-1.0M.

In some embodiments, in the step 5'), the reflux is carried out for about 40-50 hours, for example about 48 hours.

In some embodiments, step 6') is carried out in trifluoroacetic acid and dichloromethane, preferably trifluoroacetic acid:dichloromethane=3:1 (more preferably the concentration of the compound of Formula 9' in the aforementioned solvent is 0.2M) for about 30 minutes to 1 hour.

In some embodiments, the step 7''') is carried out in the presence of N-iodosuccinimide (NIS), preferably N-iodosuccinimide in an amount of 1.2 eq relative to the compound of Formula 10''', and/or in an organic solvent, preferably DMF (more preferably, the concentration of the compound of Formula 10' in the aforementioned solvent is 0.1M), and/or at 0° C. to RT.

In some embodiments, the steps 1') and 2'') are carried out in a one-pot process.

The aforementioned embodiments can be optionally combined.

Another aspect of the present invention relates to a method for preparing a compound of Formula (I) or a pharmaceutically acceptable salt thereof (hereinafter referred to as Method II), Formula (I)

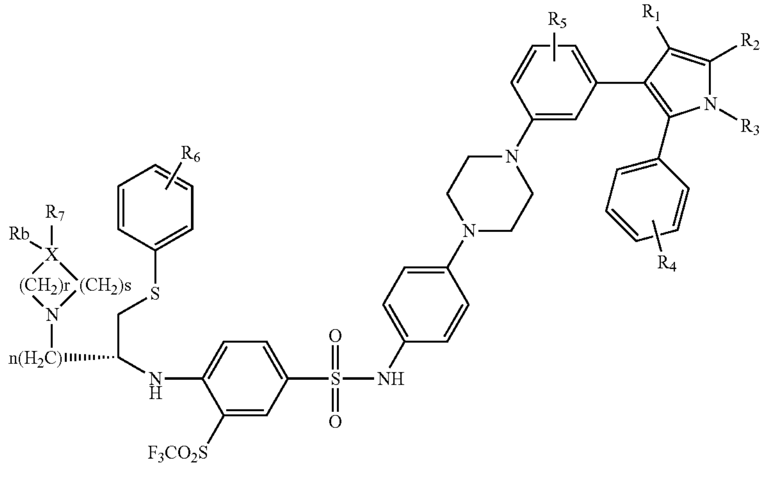

wherein, $R_1$ is SO2R', $R_2$ is an alkyl, preferably $C_{1-4}$alkyl, more preferably methyl, propyl, isopropyl, $R_3$ is an alkyl, preferably $C_{1-4}$alkyl, more preferably methyl, propyl, isopropyl, $R_4$ is a halogen, preferably fluorine, chlorine, $R_5$ is a halogen, preferably fluorine, chlorine, $R_6$ is selected from the group consisting of H, halogen, alkyl, preferably fluorine, chlorine, $C_{1-4}$alkyl, more preferably methyl, propyl, isopropyl, $R_7$ is hydroxyl, alkoxyl, preferably $C_{1-4}$alkoxyl or alkoxylcarbonyl, preferably $C_{1-4}$alkoxylcarbonyl, more preferably butoxycarbonyl, most preferably tert-butoxycarbonyl, $R_b$ is hydrogen or alkyl, preferably $C_{1-4}$alkyl, more preferably methyl, propyl, isopropyl, n, r and s independently are 1, 2, 3, 4, 5 or 6, preferably, r and s both are 2 and n is 3, 4 or 5, more preferably, n, r and s each are 2, R' is an alkyl, preferably $C_{1-4}$alkyl, more preferably methyl, propyl, isopropyl, X is carbon or nitrogen, when X is nitrogen, Rb is H, The method comprises the following steps:

(1) reacting a compound of Formula 1 with a compound of Formula 2 to form a compound of Formula I, Formula 1

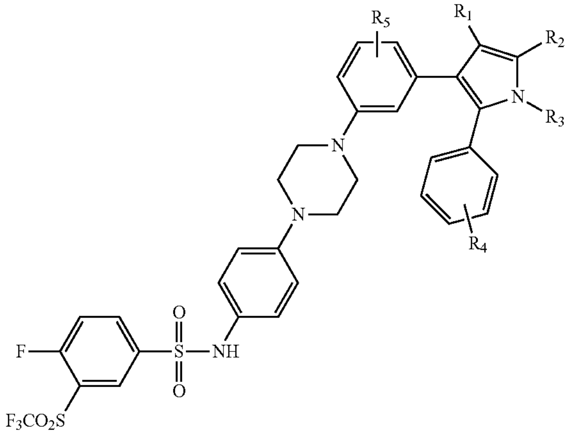

wherein, $R_1$, $R_2$, $R_3$, $R_4$ and $R_5$ each are defined as those for Formula (I);

Formula 2

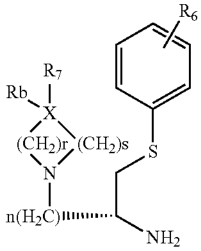

wherein, $R_5$, $R_7$, Rb, r, s and n each are defined as those for Formula (I).

In some embodiments, in the step (1), the compound of Formula 2 is about 1.5 to 3.0 eq, preferably about 1.5 to 2.0 eq, relative to 1 molar equivalent of the compound of Formula 1.

In some embodiments, the step (1) is carried out in the presence of DIPEA, preferably DIPEA in an amount of from about 2.0 to 4.0 eq, more preferably about 3.0 eq, relative to 1 molar equivalent of the compound of Formula 1, and/or in an organic solvent, preferably DMF.

In some embodiments, preparation of the compound of Formula 1 comprises the following steps:

(1') forming a compound of Formula 1 from the compound of Formula 1',

Formula 1'

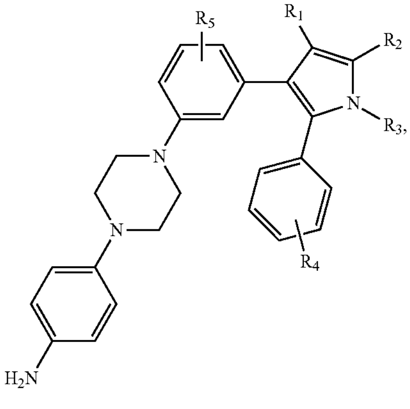

wherein, $R_1$, $R_2$, $R_3$, $R_4$ and $R_5$ each are defined as those for Formula (I).

In some embodiments, in the step (1'), the compound of Formula 1' reacts with a compound of Formula 2', Formula 2'

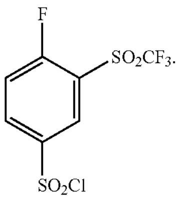

In some embodiments, the compound of Formula 2' is about 1.5 to 3.0 eq, preferably about 1.5 to 2.0 eq, relative to 1 molar equivalent of the compound of Formula 1'.

In some embodiments, the step (1') is carried out in a polar solvent, preferably tetrahydrofuran, and the concentration of the compound of Formula 1' in the aforementioned solvent is 0.1-0.5 M.

In some embodiments, the step (1') is carried out in the presence of pyridine as a base, preferably in the presence of pyridine in an amount of 2.5 eq relative to 1 molar equivalent of the compound of Formula 1'.

In some embodiments, the step (1') is carried out at a temperature of about −10° C. to 10° C., preferably in the range of about −5° C. to 5° C.

In some embodiments, preparation of the compound of Formula 1' comprises the following steps:

(1") reacting the compound of Formula 1" with an alkyl sulfonate salt (e.g., $R_1Na$) to form a compound of Formula 2", Formula 1"

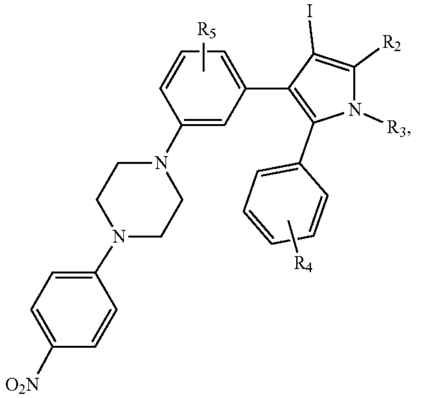

wherein, $R_2$, $R_3$, $R_4$ and $R_5$ each are defined as those for Formula (I);

Formula 2"

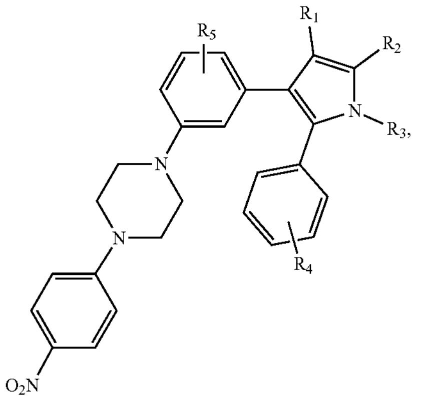

wherein, $R_1$, $R_2$, $R_3$, $R_4$ and $R_5$ each are defined as those for Formula (I).

(2") forming a compound of Formula 1' from the compound of Formula 2".

In some embodiments, in the step (1"), the alkyl sulfonate salt (for example, $R_1Na$) is used in an amount of about 10 to 15 eq relative to 1 molar equivalent of the compound of Formula 1".

In some embodiments, the step (1") is carried out in the presence of a catalyst such as a metal iodide, preferably CuI, preferably CuI in an amount of about 0.5 to 1.0 eq, preferably about 0.6 to 0.8 eq, relative to 1 molar equivalent of the compound of Formula 1", L-Proline, preferably L-Proline in an amount of 1.0-1.3 eq relative to 1 molar equivalent of the compound of Formula 1", a base such as a hydroxide, preferably an alkali metal hydroxide such as NaOH, KOH, preferably NaOH or KOH in an amount of 2.0 eq relative to the compound of Formula 1", and/or in an organic solvent, preferably DMSO, and/or at about 110-130° C., for example, about 120° C., more preferably, the concentration of the compound of Formula 1" in the aforementioned solvent is 0.2M.

In some embodiments, the step (2") uses a catalyst, preferably iron and ammonium chloride solution.

In some embodiments, the step (2") is carried out in a polar solvent, preferably ethanol.

In some embodiments, preparation of the compound of Formula 1" comprises the following steps:

(1"') reacting a compound of Formula 1"' with a compound of Formula 2"' to form a compound of Formula 3"', Formula 1"'

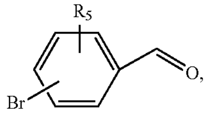

in Formula 1"', preferably phenyl ring is substituted in the meta position by $R_5$, more preferably phenyl ring is substituted in the meta positions by $R_5$ and Br, Formula 2"'

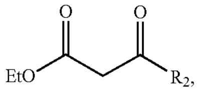

Formula 3"'

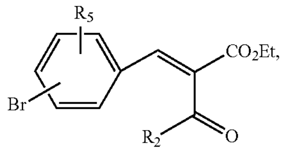

in Formula 3"', preferably phenyl ring is substituted in the meta position by $R_5$, more preferably phenyl ring is substituted in the meta positions by $R_5$ and Br, 2"') reacting the compound of Formula 3"' with a compound of Formula 4"' to form a compound of Formula 5"', Formula 4"'

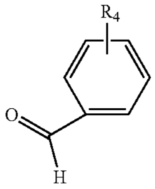

-continued

Formula 5'''

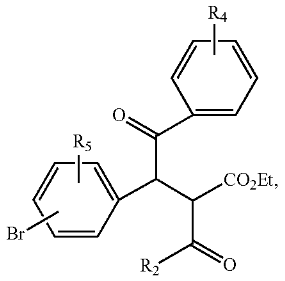

in Formula 5''', preferably phenyl ring is substituted in the meta position by $R_5$, more preferably phenyl ring is substituted in the meta positions by $R_5$ and Br, 3''') reacting the compound of Formula 5''' with a compound of Formula 6''' to form a compound of Formula 7''', Formula 6'''

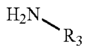

Formula 7'''

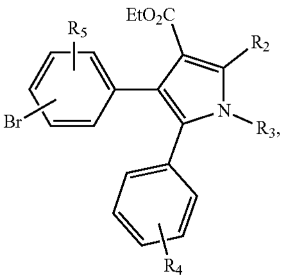

in Formula 7''', preferably phenyl ring is substituted in the meta position by $R_5$, more preferably phenyl ring is substituted in the meta positions by $R_5$ and Br, 4'''-a) forming a compound of Formula 11''' from the compound of Formula 7''', Formula 11'''

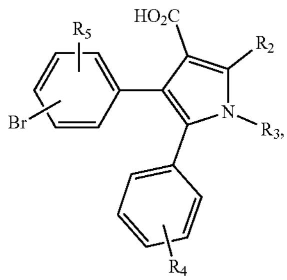

in Formula 11, preferably phenyl ring is substituted in the meta position by $R_5$, more preferably phenyl ring is substituted in the meta positions by $R_5$ and Br, 5'''-a) forming a compound of Formula 12''' from the compound of Formula 11''', Formula 12'''

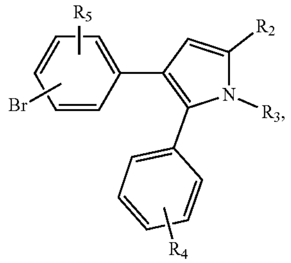

in Formula 12''', preferably phenyl ring is substituted in the meta position by $R_5$, more preferably phenyl ring is substituted in the meta positions by $R_5$ and Br, 6'''-a) forming a compound of Formula 10''' from the compound of Formula 12''', Formula 10'''

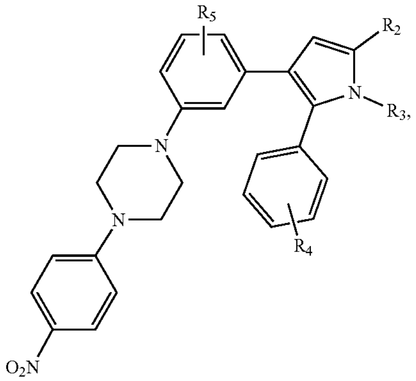

7''') forming a compound of Formula 1'' from the compound of Formula 10''',

In some embodiments, in the step 1'''), preferably, the amount of the compound of Formula 1''' is 1.0 eq, preferably, the amount of the compound of Formula 2''' is 1.1 eq.

In some embodiments, in the step 1'''), the reaction is carried out in the presence of an organic base, such as piperidine, preferably piperidine in an amount of 0.01 ml/g, and/or in the presence of AcOH, preferably AcOH in an amount of 0.03 ml/g, and/or in an organic solvent, preferably toluene, and/or under reflux, and/or for 18-20 hours, preferably, the concentration of the compound of Formula 1''' in the solvent is 1.2~1.7 M.

In some embodiments, in the step 2'''), preferably, the amount of the compound of Formula 4''' is 1 eq, relative to the compound of Formula 3'''.

In some embodiments, the step 2''') is carried out in the presence of an organic base, triethylamine, triethylamine in an amount of 2 eq relative to the compound of Formula 3''', 3-ethyl-5-(2-hydroxyethyl)-4-methylthiazolium bromide, 3-ethyl-5-(2-hydroxyethyl)-4-methylthiazolium bromide in an amount of 0.15 eq relative to the compound of Formula 3''', and/or in a polar solvent, preferably ethanol, at about 60-80° C., preferably about 70° C., for about 18-20 hours, preferably, the concentration of the compound of Formula 3' in the aforementioned solvent is 0.6~0.7M.

In some embodiments, in the step 3'''), the amount of the compound of Formula 6''' is about 8-15 eq, for example about 10 eq, relative to the compound of Formula 5'''.

The step 3''') is carried out in a polar solvent, preferably methanol.

In some embodiments, the step 3') is carried out in the presence of AcOH, preferably AcOH in an amount of about 10 eq relative to the compound of Formula 5''', and/or at about 40-70° C., for example 50° C., for about 18-20 hours.

In some embodiments, the step 4'-a) is carried out in the presence of a base such as a hydroxide, preferably an alkali metal hydroxide such as NaOH, KOH.

In some embodiments, the step 4'''-a) is carried out in a mixed solution of polar solvents, preferably 1,4-dioxane, ethanol, and water.

In some embodiments, in the step 5'-a), the amount of the compound of Formula 11' is 1.0 eq relative to the compound of Formula 7'''.

In some embodiments, the step 5'''-a) is carried out in an organic solvent, preferably a polar solvent, more preferably dichloromethane.

In some embodiments, the step 5'-a) is carried out in the presence of a strong acid such as hydrochloric acid, sulfuric acid or trifluoroacetic acid, preferably trifluoroacetic acid.

In some embodiments, in the step 6'-a), the amount of the compound of Formula 12' compound is 1.0 eq relative to the compound of Formula 7'''.

In some embodiments, in the step 6'-a), the compound of Formula 12''' reacts with 1-(nitrophenyl)piperazine, preferably 1-(nitrophenyl)piperazine in an amount of about 1.8 to 2 eq relative to the compound of Formula 7'''.

In some embodiments, the step 6'-a) is carried out in the presence of a catalyst such as a metal iodide, preferably CuI, for example, CuI in an amount of about 0.5 to 1.0 eq, preferably about 0.6 to 0.8 eq, relative to the compound of Formula 7''', [(2,6-dimethylphenyl)amino](oxo)acetic acid (DMPAO), carbonate salt, preferably sodium carbonate or potassium carbonate.

In some embodiments, the step 7''') is carried out in the presence of N-iodosuccinimide (NIS), preferably in an amount of 1.2 eq relative to the compound of Formula 10''', and/or in DMF, and/or at 0° C. to RT, and/or the concentration of the compound of Formula 10''' in the aforementioned solvent is 0.1 M.

The aforementioned embodiments can be optionally combined.

Another aspect of the invention further relates to a compound of the above Formulae, and a compound having the following structure Formula,

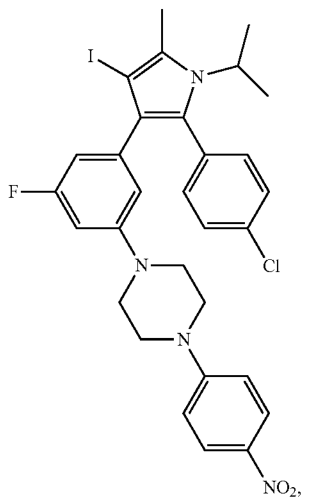

-continued

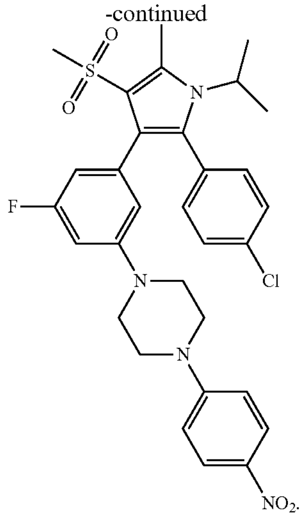

The compounds can be used as intermediates for the preparation of the compound of Formula (I).

Another aspect of the invention further relates to a use of any one of the above intermediate compounds in the preparation of the compound of Formula (I).

Effect Description

The method of the invention produces no or less toxic by-products, reduces or eliminates the use of solvents which are prone to environment pollution, reduces or eliminates the use of column chromatography purification, reduces or eliminates the use of liquid phase purification and freeze-drying operations, reduces costs, shortens cycle time, increases yield and increases batch capacity.

The final product prepared by the method of the present invention has an unexpected technical effect compared to the compounds known in the prior art. Specifically, the comparative data in the following effect tests demonstrate that the compound of Formula has unexpected technical effects in comparison with the compounds known in the prior art.

The novel final product of the present invention has unexpected technical effects of inhibiting Bcl-2 and/or Bcl-xL, and inhibiting and treating cancers.

Specifically, the comparative data in the following effect tests prove the new final product has unexpected technical effects compared to the compounds known in the prior art.

Specific Modes for Carrying Out the Invention

The present invention is further illustrated by specific preparation examples and effect experiments, but it should be understood that these examples and effect experiments are only used for illustrations in more detail and specifically, and should not be construed as any limitation to the invention.

PREPARATION EXAMPLES

Preparation Example 1

In this example, Compound 1 was prepared, and the specific preparation method comprises the following steps, and the method corresponds to Method

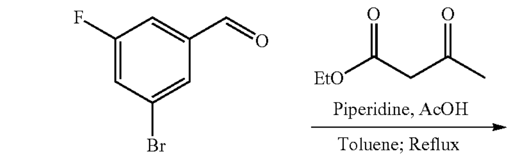
Compound 17-02A
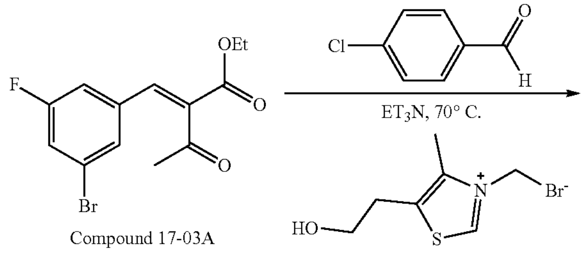
Compound 17-03A
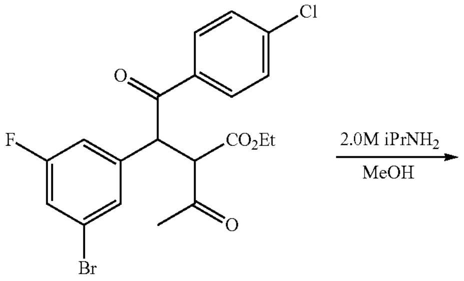
Compound 1-01A
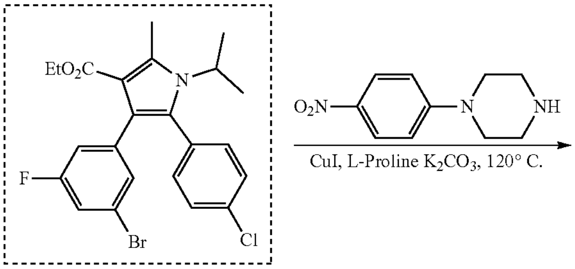
Compound 1-02A
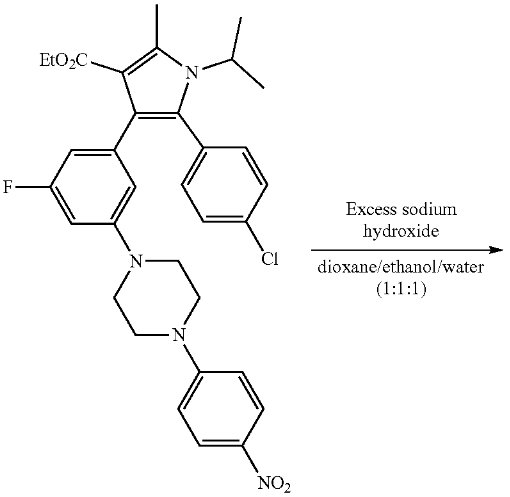
Compound 1-03A
-continued
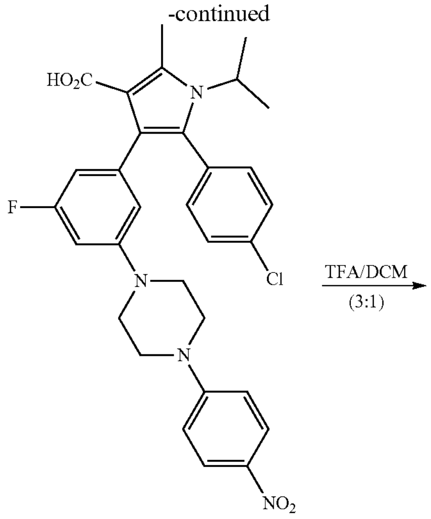
Compound 1-04A
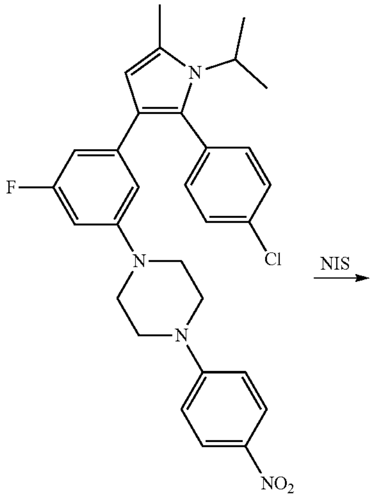
Compound 1-05A
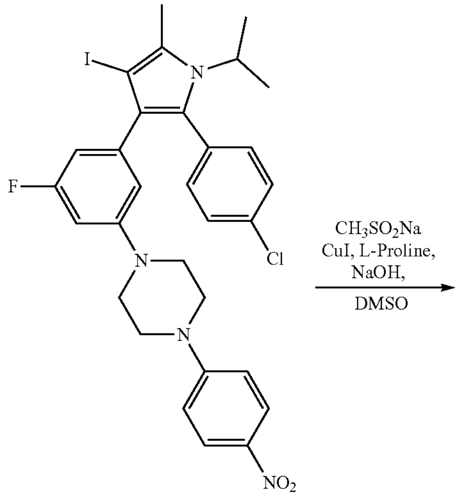
Compound 1-06A -continued

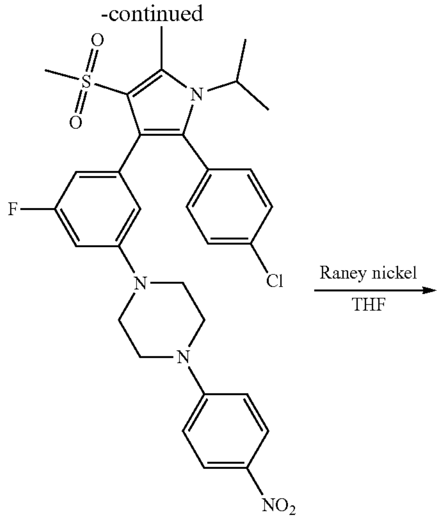

Compound 1-07A

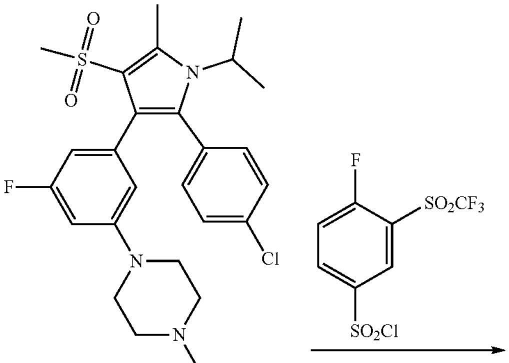

Compound 011

Compound 1-08A

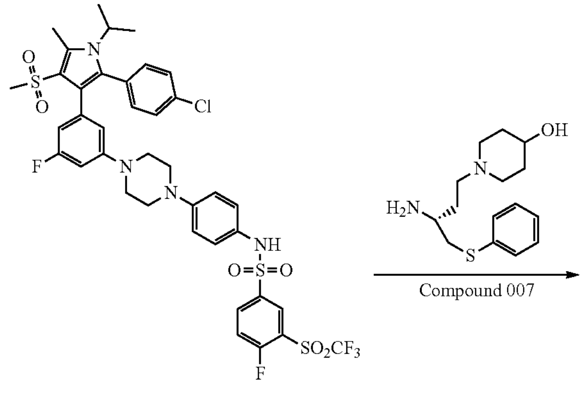

Compound 007

Compound 1-09A

-continued

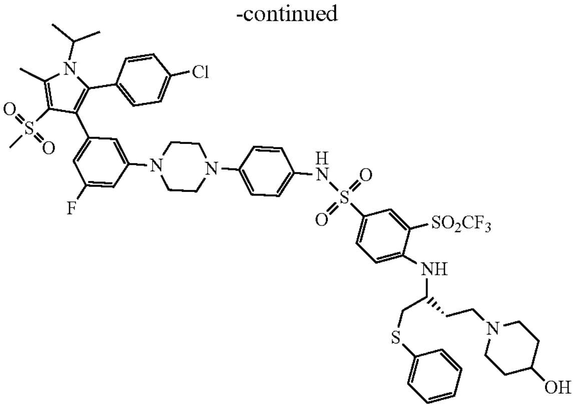

Compound 1

Preparation of Compound 17-03A 600 ml of toluene, 106.5 g of ethyl acetoacetate, 13.6 ml of acetic acid, 4.5 ml of piperidine, 150 g of 3-bromo-5-fluoro-benzaldehyde were added into a flask, and the reaction was carried out under heating and reflux to remove water for 18-20 hours, and TLC showed that the reaction was complete. The reaction mixture was added with ethyl acetate for dilution, the ethyl acetate phase was washed with 1M hydrochloric acid and water, respectively, the organic phase was dried over anhydrous magnesium sulfate, subjected to rapid column purification, and then concentrated to obtain 202 g of a colorless oil as the product, yield 86%.

Preparation of Compound 1-01A

1 L of absolute ethanol, 202 g of Compound 17-03A, 90.1 g of p-chlorobenzaldehyde, 129.5 g of triethylamine and 24.3 g of 3-ethyl-5-(2-hydroxyethyl)-4-methylthiazolium bromide were added in a flask, stirred at 70° C. overnight. TLC was used to monitor the completion of reaction of the compound 17-03A. The reaction mixture was diluted with ethyl acetate. The organic phase was washed with 1M hydrochloric acid, washed with water, saturated aqueous sodium hydrogen carbonate solution, and washed with saturated saline. The obtained organic phase was dried over anhydrous magnesium sulfate, concentrated under a reduced pressure to obtain 314 g of crude product as an oil, yield 100%. The crude product was used in the next step without further purification.

Preparation of Compound 1-02A

1 L of methanol, 194.2 g of Compound 1-01A and 255.9 g of acetic acid were added into a flask, and then 251.9 g of isopropylamine was added dropwise to the reaction mixture, and stirred at 50° C. After TLC showed that the reaction was completed, methanol was removed by concentration under reduced pressure. Ethyl acetate was added into the reaction mixture for dilution. The organic phase was washed, dried over anhydrous magnesium sulfate, concentrated under reduced pressure to obtain 106.8 g of crude product as an oil, yield 89%, which was directly used in the next step without purification.

Preparation of Compound 1-03A 46 g of Compound 1-02A, 35.8 g of 1-(4-nitro-phenyl)-piperazine, 9.2 g of CuI, 5.5 g of L-proline and 33.2 g of potassium carbonate were added into a flask, then added with 500 ml of dimethylsulfoxide, the reaction mixture was stirred at 120° C. for 18-20 hours. After TLC showed that the reaction of Compound 1-02A was complete, the reaction solution was cooled to 0° C. Ethyl acetate was added into the mixture for extracting the reaction solution. The combined organic phase was washed, dried over magnesium sulfate, concentrated under reduced pressure to obtain an oil, which was purified by column chromatography to obtain 24.2 g of product, and the total yield of the above three steps was 40%.

Preparation of Compound 1-04A 52.8 g of Compound 1-03A, 300 ml of 1,4-dioxane, 300 ml of ethanol and 300 ml of water were added into a flask, and then 174.5 g of sodium hydroxide was slowly added, and the reaction solution was refluxed for 48 hours. After TLC showed that the reaction of Compound 1-03A was complete, the reaction solution was cooled to 0° C., the pH of the reaction solution was adjusted to about 1, a large amount of solid appeared and was filtered, and the solid was dried to obtain 50.2 g of product, yield 99%.

Preparation of Compound 1-05A 39 g of Compound 1-04A was placed in a flask, then 270 ml of trifluoroacetic acid and dichloromethane were added, and the reaction mixture was stirred. After TLC showed that the reaction of Compound 1-04A was completed, the reaction mixture was extracted with dichloromethane, the organic phase was washed, dried over anhydrous magnesium sulfate and concentrated under reduced pressure to give 39 g of product, yield 91%.

Preparation of Compound 1-06A 15.4 g of Compound 1-05A, 250 ml of dimethylformamide were added into a flask, and then the mixture was cooled to 0° C. To the mixture was added 7.8 g of N-iodosuccinimide. The mixture was stirred overnight. After TLC showed that the reaction of Compound 1-05A was completed, dimethylformamide was removed by concentration under reduced pressure to give an oil. The oil was washed with a mixture solvent (ethyl acetate/n-hexane=3/1), and a large amount of solid appeared, and was filtered and dried to give 14.1 g of solid, yield 74%.

Preparation of Compound 1-07A 3.8 g of Compound 1-06A, 28 ml of dimethylsulfoxide, 5.8 g of sodium methylsulfonate, 0.65 g of cuprous iodide, 0.66 g of L-proline and 0.46 g of sodium hydroxide were added into a flask. The reaction mixture was stirred under $N_2$ and at 90° C. After TLC showed that the reaction was completed, the reaction mixture was cooled to room temperature. 50 ml of saturated ammonium chloride was slowly added to the reaction mixture. Extraction was carried by ethyl acetate. The combined organic phases were dried over anhydrous magnesium sulfate, concentrated under reduced pressure to give an oil, which was purified by column chromatography (eluent: n-hexane:ethyl acetate:dichloromethane=8:1:1; 5:1:1; 3:1:1) to give 2.5 g of a product, yield 71%.

Preparation of Compound 1-09A 10 g of Compound 1-07A, 150 ml of tetrahydrofuran and 10 g of Raney nickel were added into a flask, and the reaction mixture was stirred at room temperature under hydrogen gas. After TLC showed that the reaction was completed, Raney nickel was removed by filtration, and the filtrate (containing Compound 1-08A) was used in the next step without further purification. 8.0 g of the filtrate, 150 ml of dichloromethane, and 3.16 g of Compound 011 were added into a flask. The reaction mixture was stirred at −5° C. After TLC showed that the reaction of Compound 1-08A was completed, dichloromethane was added for dilution, then washed with water and saturated saline, respectively, dried over anhydrous magnesium sulfate and concentrated under reduced pressure. The obtained oil was purified by column purification to give 10.5 g of product, yield 73%.

The intermediate Compound 007 to which the present invention relates was produced by the following method:

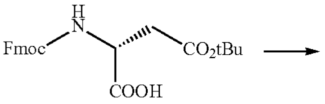

compound 007-n

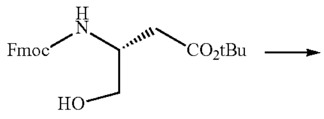

compound 007-01A

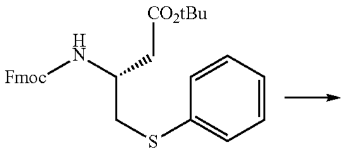

compound 007-02A

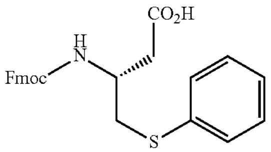

compound 007-03A

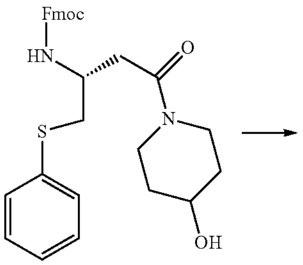

compound 007-04A

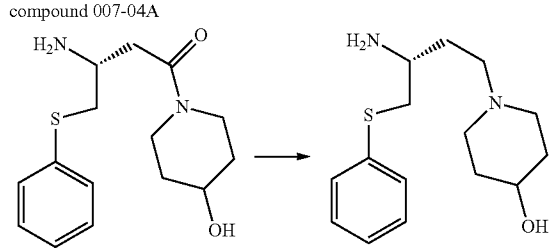

compound 007-05A compound 007

Synthesis of Compound 007-01A

A solution of Compound 007-n (1.0 eq.) and N-methylmorpholine (1.1 eq.) in ethylene glycol dimethyl ether was cooled to −15° C., and isobutyl chloroformate (1.0 eq.) was slowly added. After that, it was raised to 0° C. over about 30 minutes. The precipitated N-methylmorpholine hydrochloride was removed by filtration, and the filter cake was washed with ethylene glycol dimethyl ether. The filtrate and washing solution were combined in a large flask, and cooled to −15° C. An aqueous solution of sodium borohydride (5.0 eq.) was added to the reaction solution to generate a large amount of gas, water was added immediately to precipitate a large amount of white solid, which was filtered and dried under vacuum to give Compound 007-01A as white solid.

Synthesis of Compound 007-02A

To a solution of tributylphosphine (2.0 eq.) and Compound 007-01A (1.0 eq.) in dichloromethane, diphenyldisulfide (2.0 eq.) was added and the reaction mixture was stirred at room temperature for 24 hours. After TLC showed the completion of the reaction, the reaction mixture was washed three times with water until the pH of the aqueous phase was about 7. The dichloromethane phase was dried over anhydrous sodium sulfate, filtered and concentrated under reduced pressure to remove solvent to give a residue (oil) as a crude product of 007-02A.

Synthesis of Compound 007-03A

The above crude product of Compound 007-02A was dissolved in dichloromethane, and trifluoroacetic acid was added to the solution. The reaction mixture was stirred at room temperature overnight. After TLC showed that the reaction was completed, the reaction mixture was washed with water. The dichloromethane was dried over anhydrous sodium sulfate, then dichloromethane was removed to give a large amount of white solid, which was filtrated. The obtained white solid was washed twice with a mixture solvent (ethyl acetate hexane=1:6) and filtrated to obtain Compound 007-03A.

Synthesis of Compound 007-04A

To a solution of Compound 007-03A (1.0 eq.) in dichloromethane, oxalyl chloride and some dimethylformamide were added at 0° C. The reaction mixture was stirred at room temperature for about 2 hours. After TLC showed that the reaction was completed, solvent was removed under reduced pressure. The residue was dissolved in dichloromethane, cooled to 0° C., added with a solution of piperidine-4-ol (1.5 eq.) in dichloromethane at 0° C., the pH of the reaction mixture was adjusted with piperidin-4-ol to 8-9, and the reaction solution was stirred at 0° for 10-20 minutes. After TLC showed that the reaction was completed, the reaction mixture was washed with 1N hydrochloric acid, water and saline, respectively. After layering, the obtained organic phase was dried over sodium sulfate and filtrated, the filtrate was desolvated under reduced pressure, and purified by column chromatography to obtain the target compound.

Synthesis of Synthetic 007-05A

A solution of BCI-007-04A (1.0 eq) in acetonitrile was treated with diethylamine (20 eq) under stirring. After TLC showed that the reaction was completed, the reaction mixture was concentrated to obtain a residue. The residue was used in the next step without further purification.

Synthesis of Compound 007

A mixture of Compound 007-05A (1.0 eq) and 1 M borane in tetrahydrofuran was stirred at room temperature. After TLC showed that the reaction was completed, the pH of the solution was then adjusted to 10 with 4N aqueous potassium carbonate solution. The mixture was extracted for three times with dichloromethane. The organic phase was dried over anhydrous sodium sulfate. The solvent was removed under reduced pressure to give residue. The residue was purified by column chromatography to obtain the target compound (Compound 007).

Preparation of Compound 1

10.5 g of Compound 1-09A, 5.9 g of Compound 007, 4.5 g of N,N-diisopropylethylamine were added into a flask. To the reaction mixture was added 90 ml of dimethylformamide, and the reaction mixture was stirred at room temperature. After TLC showed that the reaction of Compound 1-09A was completed, the solvent was removed under reduced pressure to give a residue, which was purified by column chromatography to give 11.6 g of Compound 1, yield 85%.

The nuclear magnetic data of Compound 1 were as follows: $^1$HNMR (400 MHz, DMSO-d6) δ 9.77 (s, 1H), 7.80 (d, J=2 Hz, 1H), 7.58 (dd, J1=1.6, J2=8.0 1H), 7.38 (d, J=8.8 2H), 7.30-7.16 (m, 7H), 6.97-6.84 (m, 6H), 6.57 (d J=12, 1H), 6.53 (s, 1H), 6.37 (d J=8, 1H), 4.54 (bra, 1H), 4.36-4.29 (m, 1H), 4.03 (bra, 1H), 3.4-3.5 (m, 5H), 3.30-3.32 (m, 1H), 3.14-3.08 (m, 8H), 2.9 (s, 3H), 2.67 (s, 3H), 2.41-1.60 (m, 9H), 1.36 (s, 3H), 1.34 (s, 3H), 1.28-1.26 (m, 2H), m/z (M+1): 1131.0.

Preparation Example 2

In this example, Compound 1 was prepared, and the specific preparation method comprises the following steps, and the method corresponds to Method II:

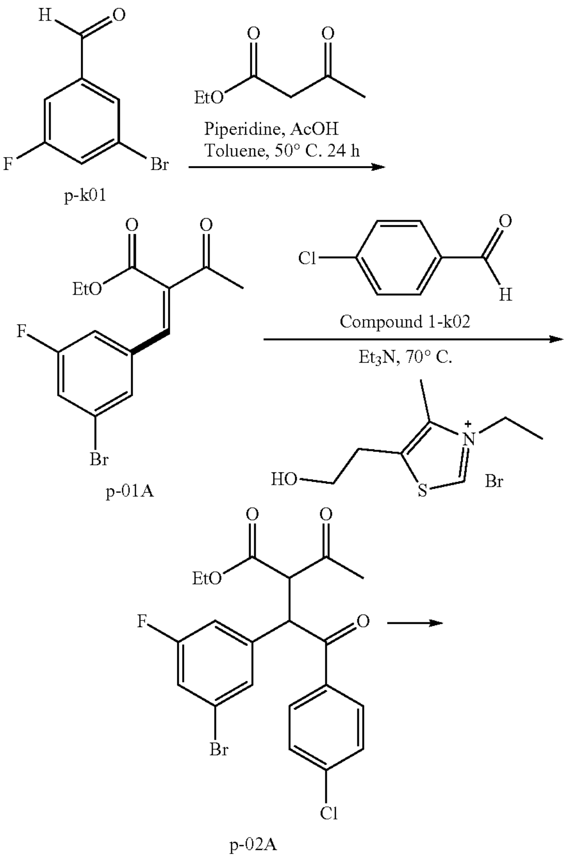

p-k01
Compound 1-k02
p-01A
p-02A

-continued
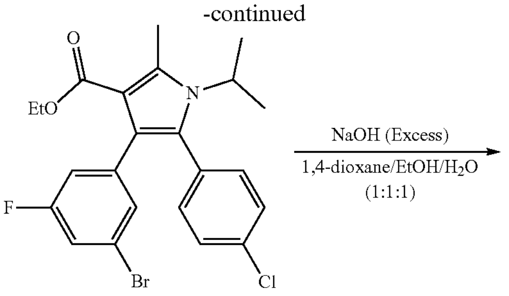
p-03A
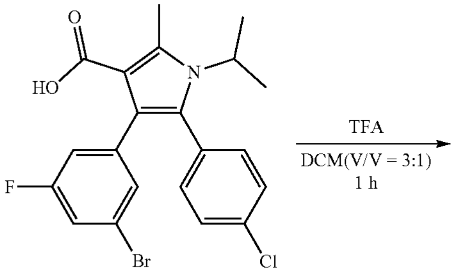
p-04B
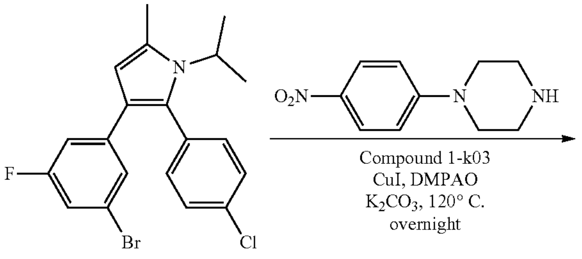
p-05B
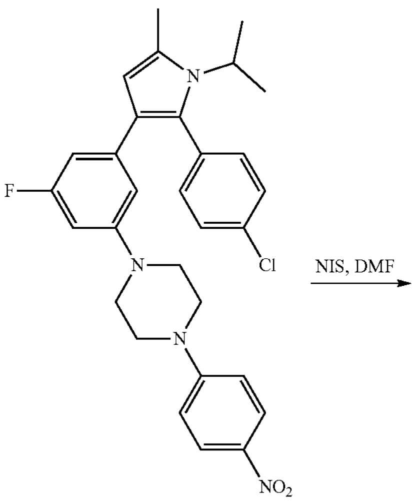
p-06A
-continued
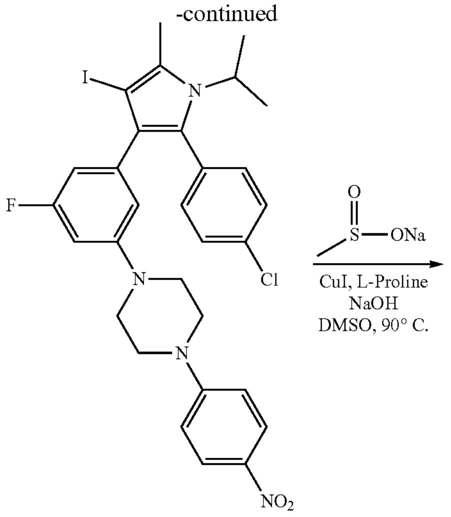
p-07A
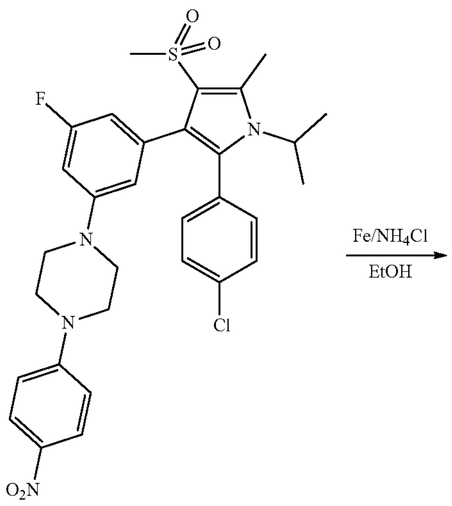
p-08A
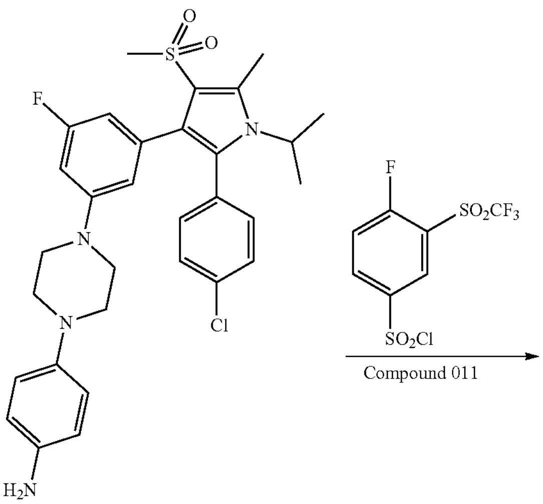
p-09A -continued

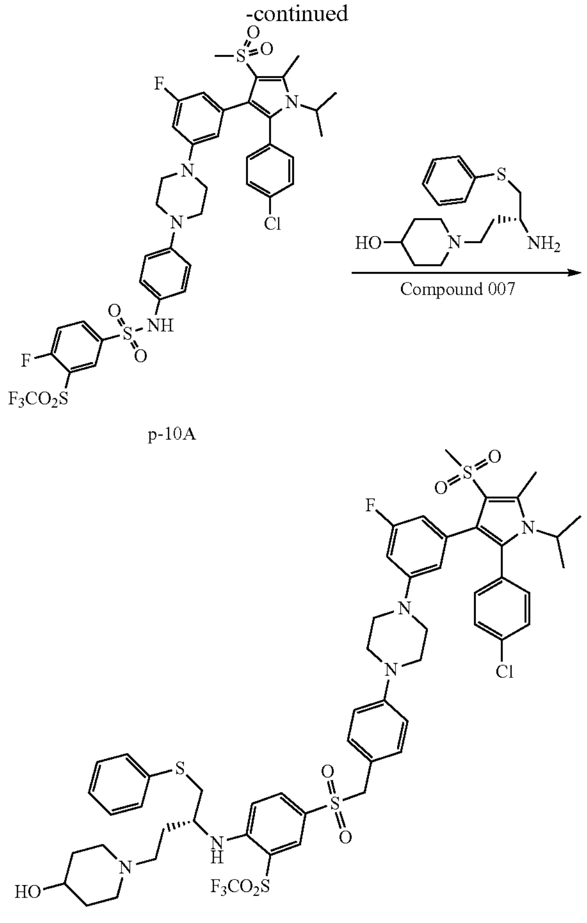

Compound 1

Step 1: Preparation of p-01A

The materials p-k01 (75 g), ethyl acetoacetate (52.9 g), piperidine (2.6 mL), acetic acid (8 mL) were added to toluene (270 L), and heated to reflux to remove water formed in the reaction. TLC monitored the reaction until the material p-k01 disappeared, then the reaction system was cooled to room temperature, diluted with ethyl acetate (150 mL). The organic phase was washed, dried over magnesium sulfate, filtered and concentrated to give a brown-red oil as a crude product, and the crude product was directly used in the next reaction.

Step 2: Preparation of p-02A

The crude p-01A obtained in the Step 1 (1131.2 g) was added to absolute ethanol (515 g), followed by adding 1-k02 (58.4 g), triethylamine (84.2 g), 3-ethyl-5-(2-hydroxyethyl)-4-methylthiazolium bromide (15.7 g) in sequence, and feeding nitrogen gas, the system was heated to 702° C., and stirred. TLC monitored the reaction until the material p-01A disappeared, the reaction system was cooled to room temperature, diluted with ethyl acetate, the organic phase was washed, dried over anhydrous magnesium sulfate, and then filtered to give a brown-red oil as a crude product, which was directly used in the next step.

Step 3: Preparation of p-03A

The crude product of p-02A obtained in the Step 2 (181.5 g) was added to methanol (1.10 L), followed by adding isopropylamine (235.4 g), acetic acid (239.0 L) in sequence, and feeding nitrogen gas, the system was heated to 50±2° C., and stirred while keeping the same temperature. TLC monitored the reaction until the material p-02A disappeared, the reaction system was cooled to room temperature, concentrated under reduced pressure, diluted with ethyl acetate; the organic phase was washed, dried over anhydrous magnesium sulfate, and then filtered and concentrated to give a crude product. The crude product was subjected to column chromatography with a system of petroleum ether and ethyl acetate to give 40 g of white solid. (the yield of the first three steps was 23%).

$^1H$ NMR (400 MHz, DMSO-$d_6$) δ 7.49-7.36 (m, 2H), 7.31-7.23 (m, 3H), 7.02 (s, 1H), 6.83 (ddd, J=10.0, 2.5, 1.3 Hz, 1H), 4.28 (p, J=7.0 Hz, 1H), 3.98 (q, J=7.1 Hz, 2H), 2.65 (s, 3H), 1.34 (d, J=7.1 Hz, 6H), 0.95 (t, J=7.1 Hz, 3H).

Step 4: Preparation of p-04B p-03A (40 g) was added to a mixed solution of 1,4-dioxane (200 mL), ethanol (200 mL) and water (200 mL), then added with sodium hydroxide (133.7 g), heated to reflux, and stirred while keeping the same temperature. TLC monitored the reaction until the material p-03A disappeared, the reaction system was cooled to room temperature, the pH value of the system was adjusted to 1-2. After filtration, the filter cake was washed thoroughly with water, and the solid was vacuum dried to obtain a white solid p-04B, which was directly used in the next reaction.

Step 5: Preparation of p-05B

The crude product of p-04B (37.84 g) was added to a mixed solution of dichloromethane (56 mL) and trifluoroacetic acid (168 mL), and nitrogen was introduced under stirring at room temperature. TLC monitored the reaction until the material p-04B disappeared, the system was added with dichloromethane for dilution, added with water, stirred for 0.5 hour, and then was allowed to stand to separate into layers. The aqueous phase was extracted with dichloromethane. The organic phase was combined, washed, dried over anhydrous magnesium sulfate, filtered and concentrated. The obtained crude product was directly used in the next reaction.

$^1H$ NMR (400 MHz, DMSO-$d_6$) δ 7.64-7.46 (m, 2H), 7.43-7.24 (m, 2H), 7.20-7.09 (m, 1H), 6.94 (t, J=1.6 Hz, 1H), 6.72 (ddd, J=10.8, 2.4, 1.4 Hz, 1H), 6.24 (d, J=1.0 Hz, 1H), 4.16 (hept, J=7.0 Hz, 1H), 2.45-2.27 (m, 3H), 1.32 (d, J=7.0 Hz, 6H).

Step 6: Preparation of p-06A

The crude product p-05B (34.0 g) of the above step was added to dimethylsulfoxide (340 mL), followed by adding 1-(nitrophenyl)piperazine (51.96 g), CuI (7.96 g), [(2,6-dimethylphenyl)amino](oxo)acetic acid (DMPAO) (16.15 g), potassium carbonate (46.21 g) in sequence, the reaction system was protected with nitrogen gas, heated to 120±5° C., and stirred while keeping the same temperature. TLC monitored the reaction until the reaction of the starting material was completed, the temperature was lowered to room temperature, and the reaction was quenched by adding a saturated ammonium chloride solution. The aqueous phase was extracted with ethyl acetate for multiple times until the aqueous phase was substantially free of product. The organic phase was combined, washed, dried over anhydrous magnesium sulfate, filtered and concentrated to obtain a crude product. The crude product was purified by column chromatography with a system of petroleum ether, ethyl acetate, dichloromethane to give 27.33 g of a yellow solid (the yield of these three steps was 61%).

$^1H$ NMR (400 MHz, DMSO-$d_6$) δ 8.16-7.97 (m, 2H), 7.58-7.44 (m, 2H), 7.39-7.18 (m, 2H), 7.09-6.94 (m, 2H), 6.46 (dt, J=12.5, 2.3 Hz, 1H), 6.37-6.29 (m, 1H), 6.27-6.12 (m, 2H), 4.18 (hept, J=7.0 Hz, 1H), 3.55-3.45 (m, 4H), 3.18-3.05 (m, 4H), 2.45-2.26 (m, 3H), 1.32 (d, J=7.0 Hz, 6H).

Step 7: Preparation of p-07A p-06A (27.33 g) was added into N,N-dimethylformamide (274 mL), fed with nitrogen gas, then the system was cooled to 0±5° C., added with N-iodosuccinimide (12.71 g), and, after cooling was stopped, was stirred continuously. TLC monitored the reaction until the material p-06A disappeared, the reaction liquid was concentrated to dry, and the crude product was added to a mixture of petroleum ether and ethyl acetate (v/v=3/1), stirred at room temperature for 2 hours, filtered, the filtrate cake was washed, and the solid was dried under vacuum to give a yellow solid p-07A (yield: 72%).

$^1H$ NMR (400 MHz, DMSO-$d_6$) δ 8.09 (d, J=9.4 Hz, 2H), 7.50-7.35 (m, 2H), 7.33-7.20 (m, 2H), 7.06 (d, J=9.5 Hz, 2H), 6.59 (d, J=12.4 Hz, 1H), 6.42 (d, J=2.1 Hz, 1H), 6.22 (d, J=9.2 Hz, 1H), 4.25 (p, J=6.9 Hz, 1H), 3.55 (t, J=5.3 Hz, 4H), 3.23 (t, J=5.2 Hz, 4H), 2.45 (s, 3H), 1.34 (d, J=7.0 Hz, 6H).

Step 8: Preparation of p-08A p-07A (47.7 g) was added to dimethylsulfoxide (496 mL), followed by adding sodium methylsulfonate (73.8 g), CuI (8.3 g), L-proline (8.3 g), sodium hydroxide (5.8 g) in sequence, the reaction system was protected by nitrogen gas, heated to 1005° C., stirred while keeping the same temperature. TLC monitored the reaction until the reaction of the raw material was completed, the reaction system was cooled to room temperature, and quenched by adding a saturated ammonium chloride solution. The aqueous phase was extracted with ethyl acetate for several times until the aqueous phase was substantially free of product. The organic phases were combined, washed, dried over anhydrous magnesium sulfate, filtered and concentrated to give a crude product. The crude product was subjected to column chromatography with a system of petroleum ether, ethyl acetate and dichloromethane, to obtain 22.64 g of yellow solid (yield: 51%)

$^1H$ NMR (400 MHz, DMSO-$d_6$) δ 8.14-8.00 (m, 2H), 7.47-7.36 (m, 2H), 7.34-7.26 (m, 2H), 7.12-6.95 (m, 2H), 6.67-6.51 (m, 2H), 6.45-6.32 (m, 1H), 4.34 (p, J=7.0 Hz, 1H), 3.62-3.47 (m, 4H), 3.25 (dd, J=6.8, 3.9 Hz, 4H), 2.92 (s, 3H), 2.69 (s, 3H), 1.36 (d, J=7.1 Hz, 6H).

Step 9: Preparation of p-09A p-08A (227 g) was added to ethanol (684 g), followed by adding ammonium chloride solution (300.8 g), iron powder (72.6 g) in sequence, the reaction was carried out under refluxing. TLC monitored the reaction until the material p-08A disappeared. The reaction system was cooled to 405° C., then added with dichloromethane (750 mL), filtered, concentrated, and the obtained solid was dried under vacuum to obtain 212.5 g of light-yellow solid (yield: 98%).

$^1H$ NMR (400 MHz, DMSO-$d_6$) δ 7.41 (d, J=8.1 Hz, 2H), 7.29 (d, J=8.0 Hz, 2H), 6.73 (d, J=8.2 Hz, 2H), 6.56 (d, J=24.3 Hz, 4H), 6.38 (d, J=9.2 Hz, 1H), 4.64 (s, 2H), 4.34 (p, J=7.1 Hz, 1H), 3.15 (t, J=4.7 Hz, 4H), 2.93 (d, J=17.6 Hz, 7H), 2.68 (s, 3H), 1.36 (d, J=7.0 Hz, 6H).

Step 10: Preparation of p-10A

The material Compound-011 (234.1 g) and pyridine (85.0 g) were added to dichloromethane (1.67 L), the system was cooled to −5±5° C., then added dropwise with pre-made solution of p-09A (208.2 g) in dichloromethane (6.25 L); after the end of the dropwise addition, the temperature was maintained at −5±5° C. under stirring. HPLC monitored the reaction until the material p-09A disappeared, the reaction liquid was washed, dried over anhydrous magnesium sulfate, filtered and concentrated, the obtained crude product was subjected to column chromatography with a system of n-heptane, ethyl acetate and dichloromethane to give 228.02 g of pale-yellow solid (yield: 73%).

$^1H$ NMR (400 MHz, DMSO-$d_6$) δ 10.15 (s, 1H), 8.33-8.12 (m, 2H), 7.92 (dd, J=9.9, 8.8 Hz, 1H), 7.45-7.22 (m, 4H), 6.96-6.81 (m, 4H), 6.67-6.48 (m, 2H), 6.39 (ddd, J=9.2, 2.1, 1.2 Hz, 1H), 4.34 (p, J=7.1 Hz, 1H), 3.13 (tq, J=11.5, 7.1, 5.4 Hz, 8H), 2.91 (s, 3H), 2.68 (s, 3H), 1.35 (d, J=7.0 Hz, 6H).

Step 11: Preparation of Compound 1 p-10A (180 g) was added to N,N-dimethylformamide (2 L), then added with Compound-007 (63.7 g) and diisopropylethylamine (80.1 g), fed with nitrogen gas, stirred at room temperature. HPLC monitored the reaction until the material p-10A disappeared, then the reaction solution was directly concentrated to dryness. The crude product was dissolved in dichloromethane, washed with 1N hydrochloric acid, saturated sodium hydrogen carbonate solution, water, and saturated sodium chloride solution in sequence, dried over anhydrous magnesium sulfate, filtered and concentrated to give light yellow solid as Compound 1 (yield: 86%).

The NMR data of Compound 1 prepared here were in coincidence with the data of Example 1.

Effect Test

The synthesis method of the invention reduces steps. The reagents, solvents and temperature used in the method greatly reduces the production cost, shortens the production cycle, increases the yield, and increases the batch capacity.

Proofs for the effects of the preferable reaction conditions of the various steps of the present invention.

1. Corresponding to the preferable reaction conditions for the preparation of Compound 1-07A from Compound 1-06A in Method I above.

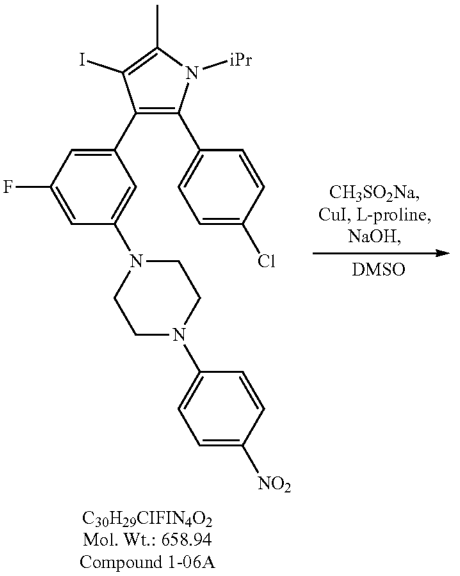

$C_{30}H_{29}ClFIN_4O_2$
Mol. Wt.: 658.94
Compound 1-06A

-continued

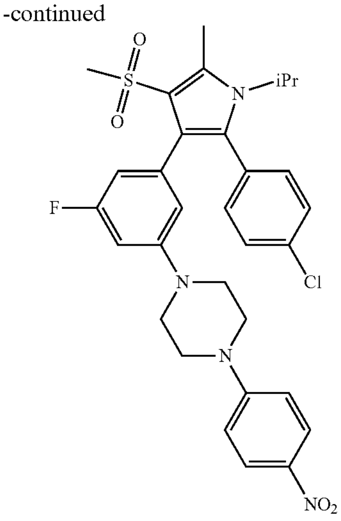

$C_{31}H_{32}ClFN_4O_4S$
Mol. Wt.: 611.13
Compound 1-07A

Three batches of tests numbered 1-1, 1-2 and 1-3 were carried out, wherein the specific reaction procedures of the test 1-1 were identical to those for the preparation of Compound 1-07A from Compound 1-06A in Preparation Example 1; the reaction operations used in tests 1-2 and 1-3 were similar to those for the preparation of Compound 1-07A from Compound 1-06A in Preparation Example 1, except that the reaction temperatures were 130° C. and 180° C., respectively. The results showed that the yield of the test 1-1 was 71%, while the yields of tests 1-2 and 1-3 were 59% and 19%, respectively.

The above data show that the yield of test 1-1 is the highest, nearly three times that of the worst batch, which confirms the reaction conditions used in test 1-1 show an unexpected technical effect.

2. Corresponding to the preferable reaction conditions for the preparation of Compound 1-09A from Compound 1-07A in Method I above.

Two batches of tests numbered 2-1 and 2-2 were carried out, wherein the specific reaction procedures of test 2-2 were identical to those for preparing Compound 1-09A from Compound 1-07A in Preparation Example 1 above, and the operations of test 2-1 were similar to those for preparing Compound 1-09A from Compound 1-07A in Preparation Example 1, except that pyridine was used in the preparation of Compound 1-08A from Compound 1-07A, and tetrahydrofuran was used in the preparation of Compound 1-09A from Compound 1-07A, while such selection of solvents was exactly the same as that used in Patent 1 above.

As a result, it was found that the yield of test 2-2 was 72.9%, while the yield of test 2-1 was 50%.

The above test results demonstrate that the yield of using tetrahydrofuran and dichloromethane as the solvent in the present invention is improved by about 20% in comparison with the solvent used in the patent, which confirms that the reaction conditions of test 2-2 show unexpected technical effect.

What is claimed is:

1. A method for preparing a compound of the following Formula (I) or a pharmaceutically acceptable salt thereof, Formula (I)

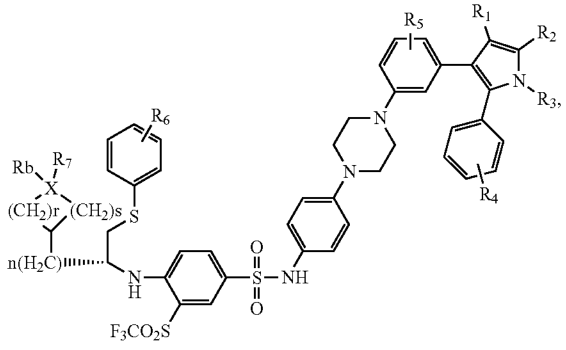

wherein, $R_1$ is $SO_2R'$, $R_2$ is $C_{1-4}$ alkyl, $R_3$ is $C_{1-4}$ alkyl, $R_4$ is halogen, $R_5$ is halogen, $R_6$ is selected from the group consisting of H, halogen, and $C_{1-4}$ alkyl, $R_7$ is hydroxyl, $C_{1-4}$ alkoxyl or $C_{1-4}$ alkoxylcarbonyl, Rb is hydrogen or $C_{1-4}$ alkyl, n, r and s each are independently 1, 2, 3, 4, 5 or 6, preferably, r and s each are 2 and n is 3, 4 or 5, more preferably, n, r and s each are 2, R' is $C_{1-4}$ alkyl, more preferably methyl, propyl, isopropyl, and X is carbon or nitrogen, wherein when X is nitrogen, then Rb is H, wherein the method comprises the following steps:

1') reacting a compound of Formula 1',

Formula 1'

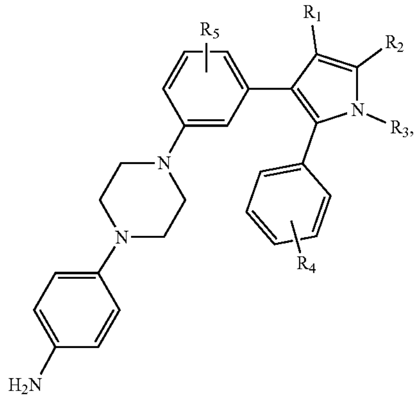

wherein $R_1$, $R_2$, $R_3$, $R_4$ and $R_5$ each are defined as for Formula (I), with a compound of Formula 2', Formula 2'

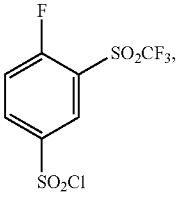

wherein $R_1$, $R_2$, $R_3$, $R_4$ and $R_5$ each are defined as for Formula (I), in a mixture of tetrahydrofuran and dichloromethane to produce a compound of Formula 1, Formula 1

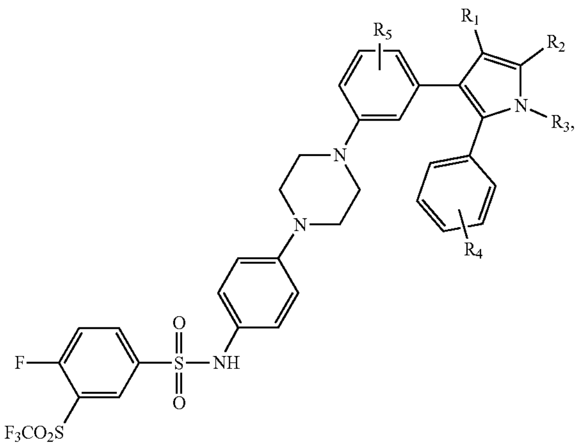

wherein $R_1$, $R_2$, $R_3$, $R_4$ and $R_5$ each are defined as for Formula (I); and 1) reacting the compound of Formula 1 with a compound of Formula 2, Formula 2

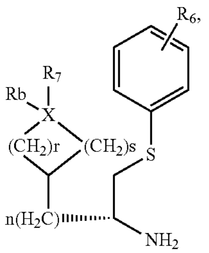

wherein $R_6$, $R_7$, Rb, X, r, s and n each are defined as for Formula (I), to produce the compound of Formula I, further comprising preparing the compound of Formula 1' by the following steps:

1") reacting a compound of Formula 1",

Formula 1"

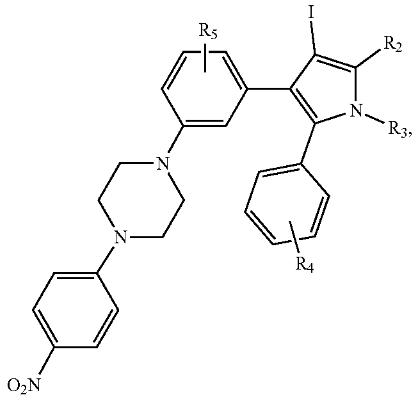

wherein $R_2$, $R_3$, $R_4$ and $R_5$ each are defined as for Formula (I), with an alkyl sulfonate salt (e.g., $R_1Na$) to produce a compound of Formula 2", Formula 2"

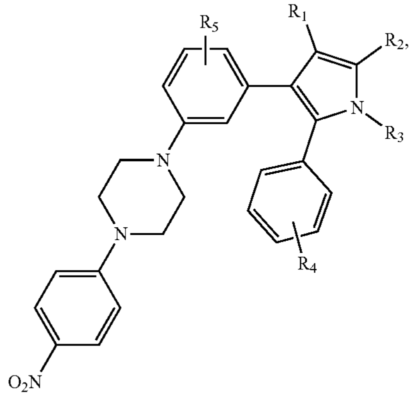

wherein $R_1$, $R_2$, $R_3$, $R_4$ and $R_5$ each are defined as for Formula (I); and 2") producing the compound of Formula 1' from the compound of Formula 2".

2. The method according to claim 1, wherein the $C_{1-4}$ alkyl of $R_2$, $R_3$, $R_6$, and Rb is independently selected from the group consisting of methyl, propyl and isopropyl; the halogen of $R_4$, $R_5$, and $R_6$ is independently selected from the group consisting of fluorine and chlorine; and the $C_{1-4}$ alkoxylcarbonyl of $R_7$ is tert-butoxycarbonyl.

3. The method according to claim 1, wherein:

in step 1), the compound of Formula 2 is in an amount of about 1.5 to 3.0 eq relative to 1 molar equivalent of the compound of Formula 1; and the reaction is carried out in the presence of a catalyst such as N,N-diisopropylethylamine (DIPEA), for example about 2.0 to 4.0 eq of DIPEA, and/or in an organic solvent such as DMF.

4. The method according to claim 1, wherein one or more of a-c apply:

a) in step 1'), the compound of Formula 2' has a molar equivalent of about 1.5 to 3.0 eq relative to 1 molar equivalent of the compound of Formula 1';

b) in step 1'), the reaction is carried out in the presence of an organic base; and c) in step 1'), the reaction is carried out at a temperature ranging from about −10° C. to 10° C.

5. The method according to claim 1, wherein one or more of a-d apply:

a) in step 1"), the alkyl sulfonate salt (for example, $R_1Na$) is used in an amount of about 10 to 15 eq, relative to 1 molar equivalent of the compound of the Formula 1";

b) in step 1"), the reaction is carried out in the presence of a catalyst such as metal iodide in an amount of about 0.5 to 1.0 eq, L-proline in an amount of about 1.0-1.3 eq, relative to 1 molar equivalent of the compound of the Formula 1", and an alkali metal hydroxide, and/or in an organic solvent, such as DMSO, at about 80-110° C., preferably at 90° C. to 100° C.;

c) in step 2"), a catalyst is used, which is selected from the group consisting of Raney nickel and iron powder; and d) in step 2"), the reaction is carried out in a polar solvent such as tetrahydrofuran.

6. The method according to claim 1 further comprising preparing the compound of Formula 1" by the following steps:

1"') reacting a compound of Formula 1"',

Formula 1"'

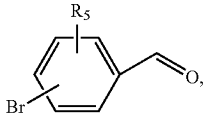

wherein $R_5$ is defined as for Formula (I), with a compound of Formula 2''',

Formula 2'''

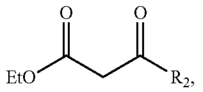

wherein $R_2$ is defined as for Formula (I), to form a compound of Formula 3''', Formula 3'''

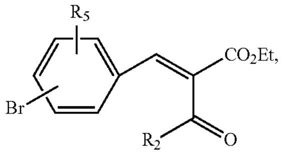

wherein $R_2$ and $R_5$ are defined as for Formula (I);

2''') reacting the compound of Formula 3''' with a compound of Formula 4''',

Formula 4'''

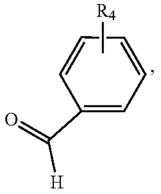

wherein $R_4$ is defined as for Formula (I), to form a compound of Formula 5''', Formula 5'''

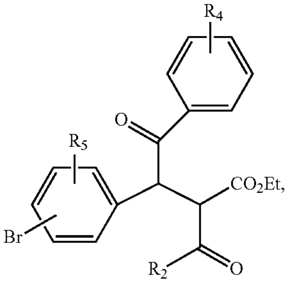

wherein $R_2$, $R_4$ and $R_5$ each are defined as for Formula (I);

3''') reacting the compound of Formula 5''' with a compound of Formula 6''',

Formula 6'''

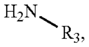

wherein $R_3$ is defined as for Formula (I), to form a compound of Formula 7''', Formula 7'''

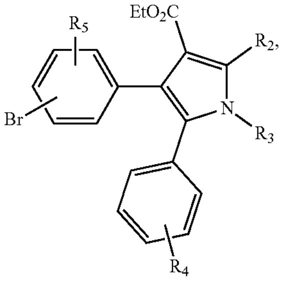

wherein $R_2$, $R_3$, $R_4$ and $R_5$ each are defined as for Formula (I);

4''') forming a compound of Formula 8''',

Formula 8'''

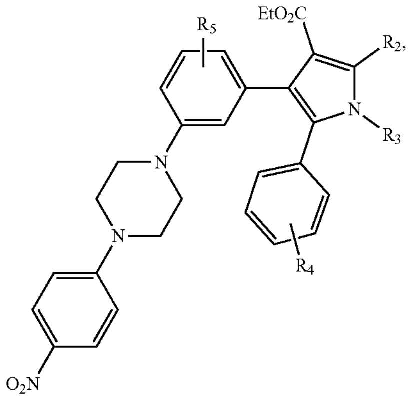

wherein $R_2$, $R_3$, $R_4$ and $R_5$ each are defined as for Formula (I), from the compound of Formula 7''';

5''') forming a compound of Formula 9''',

Formula 9'''

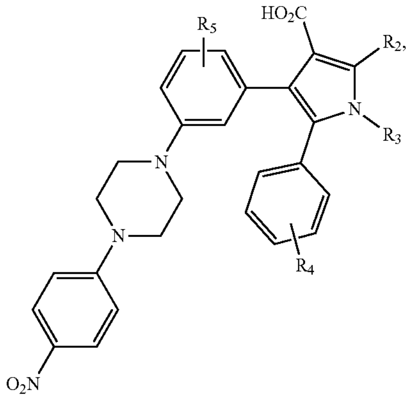

wherein $R_2$, $R_3$, $R_4$ and $R_5$ each are defined as for Formula (I), from the compound of Formula 8''';

6''') forming a compound of Formula 10''',

Formula 10'''

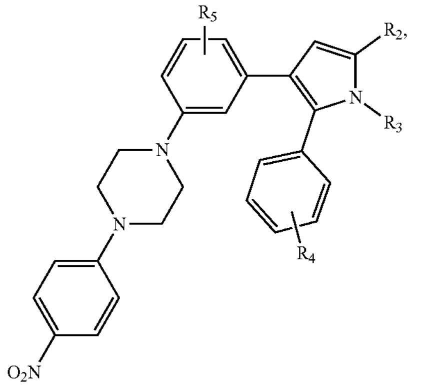

wherein $R_2$, $R_3$, $R_4$ and $R_5$ each are defined as for Formula (I), from the compound of Formula 9'''; and 7''') forming the compound of Formula 1'' from the compound of Formula 10'''.

7. The method according to claim 6, wherein, in Formula 1''', Formula 3''', Formula 5''' and Formula 7''', the phenyl ring is substituted in the meta position by $R_5$, or the phenyl ring is substituted in the meta positions by $R_5$ and Br.

8. The method according to claim 6, wherein one or more of a-n apply:

a) in step 1'''), the concentration of the compound of Formula 1''' is about 0.4 to 0.5 M;

b) in step 1'''), the reaction is carried out in the presence of an organic base such as tetrahydropyrrole, piperidine, and/or in the presence of AcOH, and/or in an organic solvent, under reflux, for about 18-20 hours;

c) in step 2'''), the reaction is carried out in the presence of an organic base, 3-ethyl-5-(2-hydroxyethyl)-4-methylthiazolium bromide, and/or in the presence of a polar solvent, at 60-80° C., preferably about 70° C., for 18-20 hours;

d) in step 3'''), the amount of the compound of Formula 6''' is 8-15 eq relative to the compound of Formula 5''';

e) step 3''') is carried out in a polar solvent, preferably methanol, ethanol, isopropanol;

f) step 3''') is carried out in the presence of AcOH, preferably in the presence of about 10 eq of AcOH relative to the compound of Formula 5''', and/or at 40-70° C., for example 50° C., for about 18-20 hours;

g) in step 4'''), the compound of Formula 7''' reacts with 1-(nitrophenyl)piperazine, preferably about 1.8 to 2 eq of 1-(nitrophenyl)piperazine relative to the compound of Formula 7''';

h) step 4''') is carried out in the presence of a catalyst such as metal iodide, L-proline, carbonate salt, and/or in an organic solvent, such as DMSO, at 110-130° C. for about 18-20 hours;

i) in step 5'''), the reaction is carried out in the presence of an excess of a base such as an hydroxide;

j) in step 5'''), the reaction is carried out in a mixed solvent such as dioxane:ethanol:water=1:1:1;

k) in step 5'''), the reaction is carried under reflux for about 40-50 hours;

l) step 6''') is carried out in TFA and DCM for about 30 minutes to 1 hour;

m) step 7''') is carried out in the presence of N-iodosuccinimide (NIS), and/or in an organic solvent, at 0° C. to RT; and n) steps 1') and 2'') are carried out in a one-pot process.

9. The method according to claim 1, further comprising preparing the compound of Formula 1'' by the following steps:

1''') reacting a compound of Formula 1''',

Formula 1'''

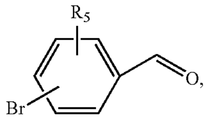

wherein $R_5$ is defined as for Formula (I), with a compound of Formula 2''',

Formula 2'''

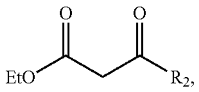

wherein $R_2$ is defined as for Formula (I), to form a compound of Formula 3''', Formula 3'''

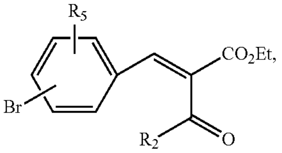

wherein $R_2$ and $R_5$ are defined as for Formula (I);

2''') reacting the compound of Formula 3''' with a compound of Formula 4''',

Formula 4'''

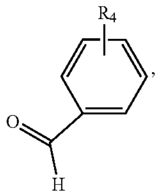

wherein $R_4$ is defined as for Formula (I), to form a compound of Formula 5''', Formula 5'''

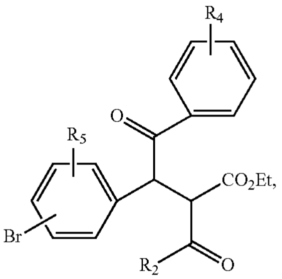

wherein $R_2$, $R_4$ and $R_5$ each are defined as for Formula (I);

3''') reacting the compound of Formula 5''' with a compound of Formula 6''',

Formula 6'''

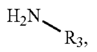

wherein $R_3$ is defined as for Formula (I), to form a compound of Formula 7''', Formula 7'''

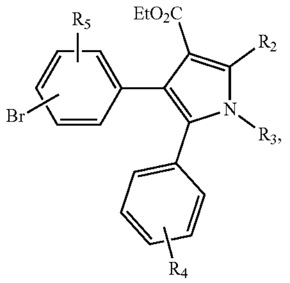

wherein $R_2$, $R_3$, $R_4$ and $R_5$ each are defined as for Formula (I);

4'''-a) forming a compound of Formula 11''',

Formula 11'''

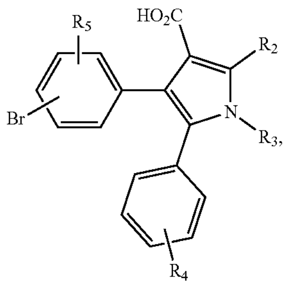

wherein $R_2$, $R_3$, $R_4$ and $R_5$ each are defined as for Formula (I), from the compound of Formula 7''';

5'''-a) forming a compound of Formula 12w,

Formula 12'''

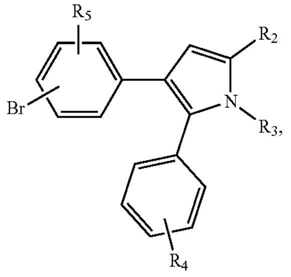

wherein $R_2$, $R_3$, $R_4$ and $R_5$ each are defined as for Formula (I), from the compound of Formula 11''';

6'''-a) forming a compound of Formula 10''',

Formula 10'''

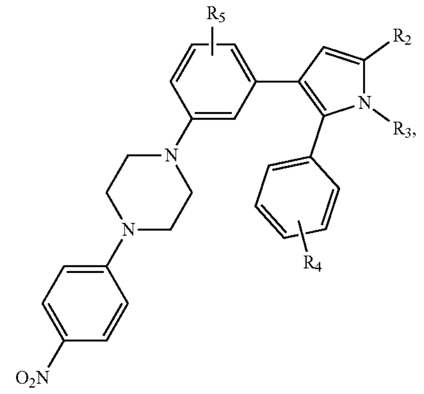

wherein $R_2$, $R_3$, $R_4$ and $R_5$ each are defined as for Formula (I), from the compound of Formula 12'''; and 7''') forming the compound of Formula 1" from the compound of Formula 10'''.

10. The method according to claim 9, wherein, in Formula 3''', Formula 5''', Formula 7''', Formula 11''' and Formula 12''', the phenyl ring is substituted in the meta position by $R_5$, or the phenyl ring is substituted in the meta positions by $R_5$ and Br.

11. The method according claim 9, wherein one or more of a-1 apply:

a) in step 1'''), the reaction is carried out in the presence of an organic base such as piperidine and/or AcOH, and/or in an organic solvent, under reflux, for 18-20 hours;

b) in step 2'''), the reaction is carried out in the presence of an organic base such as triethylamine, 3-ethyl-5-(2-hydroxyethyl)-4-methylthiazolium bromide, and/or in a polar solvent, at about 60-80° C., for 18-20 hours;

c) in step 3'''), the amount of the compound of Formula 6''' is about 8-15 eq, relative to 1 molar equivalent of the compound of Formula 5''';

d) step 3''') is carried out in a polar solvent;

e) step 3''') is carried out in the presence of AcOH, and/or at about 40-70° C., for about 18-20 hours;

f) step 4'''-a) is carried out in the presence of a base;

g) step 4'''-a) is carried out in a mixed solution of polar solvents such as 1,4-dioxane, ethanol and water;

h) step 5'''-a) is carried out in an organic solvent;

i) step 5'''-a) is carried out in the presence of a strong acid such as hydrochloric acid, sulfuric acid or trifluoroacetic acid;

j) in step 6'''-a), the compound of Formula 12''' reacts with 1-(nitrophenyl)piperazine;

k) step 6'''-a) is carried out in the presence of a catalyst such as metal iodide, [(2,6-dimethylphenyl)amino](oxo)acetic acid (DMPAO), and carbonate salt; and l) step 7''') is carried out in the presence of N-iodosuccinimide (NIS), and/or in DMF, at 0° C. to RT.

* * * * *